(12) United States Patent
Turpen et al.

(10) Patent No.: US 6,841,659 B2
(45) Date of Patent: Jan. 11, 2005

(54) METHOD FOR RECOVERING PROTEINS FROM THE INTERSTITIAL FLUID OF PLANT TISSUES

(75) Inventors: Thomas H. Turpen, Vacaville, CA (US); Stephen J. Garger, Vacaville, CA (US); Michael J. McCulloch, Vacaville, CA (US); Terri I. Cameron, Suisun, CA (US); Michelle L. Samonek-Potter, Davis, CA (US); R. Barry Holtz, Vacaville, CA (US)

(73) Assignee: Large Scale Biology Corporation, Vacaville, CA (US)

( * ) Notice: Subject to any disclaimer, the term of this patent is extended or adjusted under 35 U.S.C. 154(b) by 0 days.

(21) Appl. No.: 10/632,240

(22) Filed: Aug. 1, 2003

(65) Prior Publication Data

US 2004/0047923 A1 Mar. 11, 2004

Related U.S. Application Data

(63) Continuation of application No. 10/119,330, filed on Apr. 8, 2002, now Pat. No. 6,617,435, which is a continuation of application No. 09/726,648, filed on Nov. 28, 2000, now Pat. No. 6,441,147, which is a continuation of application No. 09/500,554, filed on Feb. 9, 2000, now Pat. No. 6,284,875, which is a continuation of application No. 09/132,989, filed on Aug. 11, 1998, now abandoned.

(51) Int. Cl.[7] .............................. C07H 1/06; C07H 1/08; C07K 1/14; C11B 1/04
(52) U.S. Cl. ....................... 530/427; 435/183; 530/344; 530/412; 536/25.41; 536/128; 554/22
(58) Field of Search ................................ 530/344, 345, 530/350, 351, 387.1, 412, 414, 417, 422, 423, 427; 536/1.11, 23.1, 25.4, 25.41, 128; 435/183, 200, 206, 208; 554/22; 562/512

(56) References Cited

U.S. PATENT DOCUMENTS

| | | | |
|---|---|---|---|
| 3,910,822 A | * 10/1975 | Pentchev et al. | ........... 435/200 |
| 3,972,777 A | * 8/1976 | Yamada et al. | ............. 435/208 |
| 4,104,125 A | * 8/1978 | Takechi et al. | ............. 435/206 |
| 4,885,248 A | 12/1989 | Ahlquist | ................... 435/172.3 |
| 5,173,410 A | 12/1992 | Ahlquist | ....................... 435/91 |
| 5,316,931 A | 5/1994 | Donson et al. | .......... 435/172.3 |
| 5,466,788 A | 11/1995 | Ahlquist et al. | ........... 536/24.1 |
| 5,500,360 A | 3/1996 | Ahlquist et al. | ......... 435/172.3 |
| 5,567,321 A | * 10/1996 | Weber et al. | ................ 210/376 |
| 5,589,367 A | 12/1996 | Donson et al. | .......... 435/172.3 |
| 5,597,569 A | * 1/1997 | Siegall et al. | ............. 424/183.1 |
| 5,602,242 A | 2/1997 | Ahlquist et al. | ......... 536/23.72 |
| 5,627,060 A | 5/1997 | Ahlquist et al. | ......... 435/172.3 |
| 5,837,826 A | * 11/1998 | Flickinger et al. | .......... 530/413 |
| 5,972,679 A | * 10/1999 | Griffith | ........................ 435/204 |
| 6,284,875 B1 | * 9/2001 | Turpen et al. | .............. 530/427 |
| 6,441,147 B1 | * 8/2002 | Turpen et al. | .............. 530/427 |
| 6,617,435 B2 | * 9/2003 | Turpen et al. | .............. 530/427 |

FOREIGN PATENT DOCUMENTS

ES    2 124 176 A1    1/1999

OTHER PUBLICATIONS

Stenesh. Dictionary of Biochemistry and Molecular Biology, Second Edition, New York: John Wiley & Sons. p. 498, 1989.*

Klement. Method of Obtaining Fluid from the Intercellular Spaces of Foliage and the Fluid's Merit as Substrate for Phytobacterial Pathogens. Phytopathological Notes. 55:1033–1034(1965).*

(List continued on next page.)

Primary Examiner—Jeffrey Edwin Russel
(74) Attorney, Agent, or Firm—Waddey & Patterson; Lucian Wayne Beavers; John C. Robbins

(57) ABSTRACT

A method for extracting proteins from the intercellular space of plants is provided. The method is applicable to the large scale isolation of many active proteins of interest synthesized by plant cells. The method may be used commercially to recover recombinantly produced proteins from plant hosts thereby making the large scale use of plants as sources for recombinant protein production feasible.

8 Claims, 8 Drawing Sheets

OTHER PUBLICATIONS

Parent et al. Detection of pathogenesis–related proteins (PR or b) and of other proteins in the intercellular fluid of hypersensistive plants infected with tobacco mosaic virus. Can. J. Bot. 62:564–569 (1984).*

Trudel et al. Expression of Active Hen Egg Lysozyme in Transgenic Tobacco. Plant Science. 87(1):55–67(1992).*

De Neve et al. Assembly of an antibody . . . Transgenic Research. 1993, vol. 2, pp. 227–237.*

Harris et al. Protein Purification Methods. Oxford: IRL Press. 1989, pp. 9, 10, 62.*

Austin et al. An Overview of a Feasibility Study for the Production of Industrial Enzymes in Transgenic Alfalfa. Annals New York Academy of Science. 721:234–244 (1994).*

De Wilde et al. Intact antigen–binding MAK23 antibody and Fab fragment accumulate in intercellular spaces of *Arabidopsis thaliana*. Plant Science. 114:223–241 (1996).*

Harris et al. Protein Purification Methods. Oxford: IRL Press. 1989, pp, 9, 10, 62.*

De Wilde et al. Intact antigen–binding MAK23 antibody and Fab fragment accumulate in intercellular spaces of *Arabidopsis thaliana*. Plant Science. 114:223–241 (1996).*

De Neve et al. "Assembly of an antibody . . . ". Transgenic Research. 1993, vol. 2, pp. 227–237.*

Harris et al. Protein Purification Methods. Oxford: IRL Press. pp. 9, 10, 62, 1989.*

Stenesh. Dictionary of Biochemistry and Molecular Biology, second edition. New York: John Wiley & Sons. p. 498, 1989.*

Bradford, M., "A Rapid and Sensitive Method for the Quantitation of Microgram Quantities of Protein Utilizing the Principle of Protein–Dye Binding," *Anal. Biochem.* 72:248–254 (1976).

Denecke et al., "Protein Secretion in Plant Cells Can Occur via a Default Pathway," *The Plant Cell* 2:51–59 (1990).

Firek et al., "Secretion of a functional single–chain Fv protein in transgenic tobacco plants and cell suspension cultures," *Plant Molecular Biology* 23:861–870 (1993).

H itz et al., "Two Apoplastic α–Amylases Are Induced in Tobacco by Virus Infection[1]," *Plant Physiol.* 97:651–656 (1991).

Herbers et al., "A Thermostable Xylanase from *Clostridium thermocellum* Expressed at High Levels in the Apoplast of Transgenic Tobacco Has No Detrimental Effects and is Easily Purified," *Bio/Technology* 13:63–66 (1995).

Jervis, L. and Pierpoint, W.S., "Purification technologies for plant proteins," *Journal of Biotechnology* 11:161–198 (1989).

Jones, R. and Robinson, D., "Transley Review No. 17 Protein secretion in plants," *New Phytology* 111:567–597 (1989).

Kinai et al., "Processing and Secretion of a Virally Encoded Antifungal Toxin in Transgenic Tobacco Plants: Evidence for a Kex2p Pathway in Plants," *The Plant Cell* 7:677–688 (1995).

Kumagai et al., "Rapid, high–level expression of biologically active α–trichosanthin in transfected plants by an RNA viral vector," *Proc. Natl. Acad. Sci. USA* 90:427–430 (1993).

Liu et al., "In vivo and in vitro activity of truncated osmotin that is secreted into the extracellular matrix," *Plant Science* 121:123–131 (1996).

Lowenthal et al., "Production of Interferon–y by Chicken T Cells," *J. Interferon and Cytokine Res.* 15:933–938 (1995).

Ma et al., "Generation and Assembly of Secretory Antibodies in Plants," *Science* 268:716–719 (1995).

Maggio et al., "Large Quantities of Recombinant PR–5 Proteins from the Extracellular Matrix of Tobacco: Rapid Production of Microbial–Recalcitrant Proteins," *Plant Molecular Biology Reporter* 14(3):249–260 (1996).

Melchers et al., "Extracellular targeting of the vacuolar tobacco proteins AP24, chitinase and β–1,3–glucanase in transgenic plants," *Plant Molecular Biology* 21:583–593 (1993).

Rathmell, W. and Sequeira, L., "Soluble Peroxidase in Fluid from the Intercellular Spaces of Tobacco Leaves," *Plant Physiol.* 53:317–318 (1974).

Regalado, A. and Ricardo, C., "Study of the Intercellular Fluid of Healthy *Lupinus albus* Organs," *Plant Physiol.* 110:227–232 (1996).

Sato et al., "Synthesis and Secretion of Tobacco Neutral PR–5 Protein by Transgenic Tobacco and Yeast," *Biochemical and Biophysical Research Communications* 211(3):909–913 (1995).

Sijmons et al., "Production of Correctly Processed Human Serum Albumin in Transgenic Plants," *Bio/Technology* 8:217–221 (1990).

Turpen et al., "Malarial Epitopes Expressed on the Surface of Recombinant Tobacco Mosiac Virus," *Bio/Technology* 13:53–57 (1995).

Van den Bulcke et al., "Characterization of vacuolar and extracellular β(1,3)–glucanases of tobacco: Evidence for a strictly compartmentalized plant defense system," *Proc. Natl. Acad. Sci. USA* 86:2673–2677 (1989).

Voss et al., "Reduced virus infectivity in *N. tabacum* secreting a TMV–specific full–size antibody," *Molecular Breeding* 1:39–50 (1995).

Trudel, J., et al. "Expression of Active Hen Egg Lysozyme in Transgenic Tobacco," *Plant Science*, 87(1):55–67 (1992).

Written Opinion of corresponding PCT Application (PCT/US99/18161), dated Jun. 21, 2000.

Response to Written Opinion of Corresponding PCT Application (PCT/US99/18161), as submitted on Sep. 20, 2000.

International Preliminary Examination of Corresponding PCT Application (PCT/US99/18161), dated Oct. 18, 2000.

* cited by examiner

BATCH VESSEL INFILTRATION

FIG. 5-A    TT01A 103L Viral cDNA

```
        |   10        |   20        |   30        |   40        |   50        |   60        |   70        |   80
   1 gtatttttac aacaattacc aacaacaaca acaacaaac acattacaa ttactattta caattacaAT GGCATACACA   80
  81 CAGACAGCTA CCCATCAGTC TTTGCTGGAC ACTGTCCGAG GAAACAACTC CTTGGTCAAT GATCTAGCAA AGCGTCGTCT  160
 161 TTACGACACA GCGGTTGAAG AGTTTAACGC TCGTGACCGC AGGCCCAAGG TGAACTTTTC AAAAGTAATA AGCGAGGAGC  240
 241 TTAAGACACA GCTTACCCGG GCGTATCCAG AATTCCAAAT TACATTTTAT AACACGCAAA ATGCCGTGCA TTCGCTTGCA  320
 321 AGACGCTTAT TGCTACTTAGA GATCTTTAGA ACTGGAATAT CTGATGATGC AAATTCCCTA CGGATCATTG ACTTATGACA TAGGCGGGAA  400
 401 TTTTGCATCG CATCTGTTCA AGGGACGAGC ATATGTACAC ACCTTTCTAG GCTAGAGAGA CCAACCTGGA CGTTGAGAC ATCATGCGGC  480
 481 ACGAAGGCCA GAAAGACAGT ATTGAACTAT GAAAATTCCT GAAGACGCTG TCTGTCACAA TACTTCCCAG CAGTCCCCAA CTTCCAAAAG  560
 561 GAAGCATTTG ACAGATACGC ATGCCATTGT GCTACACAGC TCTGTCACAA TACCTTCGGG TGAGTTCGGA ACAATGCGAC ATCAGCCGAT  640
 641 GCAGCAATCA GGCAGAGTGT TGCGCGCGAT CTTTCCACTT GCTACACAGC ATATATGACA TACCAGCCGA TGAGTTCGGG GCGGCACTCT  720
 721 TGAGGAAAAA TGTCCATACG ACGGCTGTTT TTAAGTATGT GGCAAGCAAGT GTAAGTTTTCT TGACCTTTTC CTCTAATAG CTGCTTCTTG AAGATTCATA CGTCAATTTG  800
 801 GACGAAATCA ACGGGTGTTT TTAAGTATGT GTAAGTTTTT GTAAGTTTAT ACCTGGTTTG TGACAAGT ACCTGGGTTG TAGAATAGAT TACTTCCCGG CCTCTAATAG AGAGGTTTAC ATGAAGGAGT  880
 881 TCATAGTTAT TCTAATATTC CAGAGTTAAT ACCTGGTTTC GTAAGTTTT GTAAGTTTAT AGCAATTAC GCAATTAGAT TACTTCCCGG CCTCTAATAG AGAGGTTTAC ATGAAGGAGT  960
 961 TTTTAGTCAC CAGAGTTAAT ACCTGGTTTT GTAAGTTTT GTAATTCT ATCATCATC GTGCAATGGCA ACGCATTGCT TCACAAAAAG ACTCTTGCAA TGTGCAACAG 1040
1041 AAAAGTGTAG ATAGTGAGCA CTCCTTGAGG ATTCATCATC AGTCAATTAC CGCGCAAGGA AGTCTTAGTG TGTTTCCCA AATGAGGGA TATGTCATC GTACCATTAT 1120
1121 CGAGAGAATC CTCCTTGAGG TTTGGAGACT AGTAAGAGGA CGCGCAAGGA AGTCTTAGTG TGGTTCCCA AATGAGGGA TATGTCATC GTACCATTAT 1200
1201 TCGACATTTC TTTGGAGACT CATACCAGGC GAAAGCTCTT ACATACGCAA TGGTTCCCA ATGTTTGTC CTTTGTCGAA TCGATTCGAT GTCCATGACG TTTTACCTGC 1280
1281 CACATTCGAA CATACCAGGC GTGACAGCGA GGTCCGAATG GGATGTGGAC TACTGATTAG CAAGTTAGT CTCGGTTCGA GAGGCTCTTG AAACGGTGTG CCAGCATGTG 1360
1361 CATTAACGGT GTGACAGCGA TGCCGTTCTA AAGGATGACT TACTGATTAG CAAGTTAGT CTCGGTTCGA GAGGCTCTTG AAACGGTGTG CCAGCATGTG 1440
1441 ATACTAAGCT TGCCGTTCTA AAGGATGACT GTTGGGAAC GCATTTCCCT TGATCTATAT CCGTGAAAGA GAGACCTTCC ACGACAGATT AGTGACTGAG TTATCAGAGT 1520
1521 TGGGATGAGA TTTCGCTGGC GTTGGGAAC GCATTTCCCT TGATCTATAT CCGTGAAAGA GAGACCTTCC ACGACAGATT AGTGACTGAG TACAAGGCCT 1600
1601 GGCAGGCGAC GCATTAGAGA TCAGGGTGCC TGATCTATAT AGAAGATGGA AGAAACGGAA GTGATGTACA ATGCACTTTC AGAGTTATCG 1680
1681 CTGTGGACAT GCCTGCGCTT GACATTAGGA ATTCGATGTT GATGTTTT CCCAGATGTG CTGACTCTCA CATTTGAACG ACCTACTGAG CAATGACGGC 1760
1761 GTGTTAAGGG AGTCTGACAA ATTCGATGTT TCATGAGCAA TGAGAGCGGT CAGAAGGCTT CAGAAGGCTT AGAGTTACAA TTAAGCTGGT TCGTAAGCA GATGAGCTCG ATTGTGTACA 1840
1841 AGCGAAGGTT ATAGTCGCGG TCATGAGCAA TGAGAGCGGT CAGAAGGCTT AGAGTTACAA TTAAGCTGGT TCGTAAGCA GATGAGCTCG ATTGTGTACA 1920
1921 CGCTAGCTTT ACAGGATCAA GAGAAGGCTT AGAGTTACAA TTAAGCTGGT TCGTAAGCA GATGAGCTCG ATTGTGTACA 2000
2001 AAGGGTTCGA TGGCCAGAGG AGTTTCATAT GGCAACGGCA GATTCGTTAA TTCGTAAGCA GATGAGCTCG ATTGTGTACA 2080
2081 GGAGATAGAG TCTTTAGAGC CAAATGAAAA ACTTTATGCA TAGCCTGGTA GCATCACTAT CTGCTGCGGT GTCGAATCTC 2160
2161 CGGGTCCGAT TAAAGTTCAG CAAATGAAAA ACTTTATGCA TAGCCTGGTA GCATCACTAT CTGCTGCGGT GTCGAATCTC 2240
2241 GTCAAGATCC TCAAAGATAC AGCTGCTATT GACCTTGAAA CCCGTCAAAA GTTTGGAGTC TTGGATGTTG CATCTAGGAA 2320
```

FIG. 5-B

```
2321  GTGGTTAATC AAACCAACGG CCAAGAGTCA TGCATGGGGT GTTGTTGAAA CCCACGCGAG GAAGTATCAT GTGGCGCTTT  2400
2401  TGGAATATGA TGAGCAGGGT GTGGTGACAT GCGATGATTG GAGAAGAGTA GCTGTCAGCT CTGAGTCTGT TGTTTATTCC  2480
2481  GACATGGCGA AACTCAGAAC TCTGCGCAGA CTGCTTCGAA ACGGAGAACC CGATGTCAGT AGCGCAAAGG TTGTTCTTGT  2560
2561  GGACGGAGTT CCGGGCTGTG GGAAAACCAA AGAAATTCTT TCCAGGGTTA ATTTTGATGA AGATCTAATT TTAGTACCTG  2640
2641  GGAAGCAAGC CGCGGAAATG ATCAGAAGAC GTGCGAATTC CTCAGGGATT ATTGTGGCCA CGAAGGACAA CGTTAAAACC  2720
2721  GTTGATTCTT TCATGATGAA TTTGGGAAAA AGACACAGCT GTCAGTTCAA GAGGTTATTC ATTGATGAAG GGTTGATGTT  2800
2801  GCATACTGGT TGTGTTAATT TTCTTGTGGC GATGTCATTG TGCGAAATTG CATATGTTTA CGGAGACACA CAGCAGATTC  2880
2881  CATACATCAA TAGAGTTTCA GGATTCCCGT ACCCCGCCCA TTTTGCCAAA TTGGAAGTTG ACGAGGTGGA GACACGCAGA  2960
2961  ACTACTCTCC GTTGTCCAGC CGATGTCACA CATTATCTGA ACAGGAGATA TGAGGGCTTT GTCATGAGCA CTTCTTCGGT  3040
3041  TAAAAGTCT GTTTCGCAGG AGATGGTCGG CGGAGCCGCC GTGATCAATC CGATCTCAAA ACCCTTGCAT GGCAAGATCC  3120
3121  TGACTTTTAC CCAATCGGAT AAAGAAGCTC TGCTTTCAAG AGGTATTCA GATGTTCACA CTGTGCATGA AGTGCAAGGC  3200
3201  GAGACATACT CTGATGTTTC ACTAGTTAGG TTAACCCCTA CAACCAGTCTC CATCATTGCA GGAGACAGCC CACATGTTTT  3280
3281  GGTCGCATTG TCAAGGCACA CCTGTTCGCT CAAGTACTAC ACTGTTGTTA TGGATCCTTT AGTTAGTATC ATTAGAGATC  3360
3361  TAGAGAAACT TAGCTCGTAC TTGTTAGATA TGTATAAGGT CGATGCAGGA ACACAATAGC AATTACAGAT TGACTCGGTG  3440
3441  TTCAAAGGTT CCAATCTTT TGTTGCAGCG CCAAAGACTG GTGATATTTC ACCATGAGGT TGACTGACAT TTTTACTATG ATAAGTGTCT  3520
3521  CCCAGGCAAC AGCACCATGA TGAATAATTT TGATGCTGTT CGCCTAAGGA TCAAATCAAA CCACTAATAC TTCATTGAAT GTCAAAGATT  3600
3601  GCATATTGGA TATGTCTAAG TCTGTTGCTG AATTTAGTGG CGATGATTAA AAGGAACTTT CTATGGTACG AACGGCGGCA AGTTGTCTGG  3680
3681  GAAATGCCAC GCCAGACTGG ACTATTGGAA ACTGTGCAGT AGTTGTAGAT AAGTTATTTT AACGCACCCG GCTTAAAGAA AAAGAAAAC  3760
3761  CATCATTGAT ATTGAAAATA CTGCATCTTT TTCAGTAGAG AGTCTCTCAA TAGATGGTTA GAAAAGCAGG AACAGGTAAC AATAGGCCAG  3840
3841  CAAATAAAAA TGTTTCTTTG TTCAGTAGAG AGTCTCTCAA GCAGTTGCCA GCAGTTGATC AGTACAGACA CATGATTAAA GCACAACCCA AGCAAAATT  3920
3921  CTCGCAGATT TTGATTTTGT AGATTTGCCA AGTACCCGGC ATTGTGTACC ATTCAAAAAA GATCAATGCA ATATTTGGCC  4000
4001  GGACACTTCA ATCCAAACGG AGTACCCGGC TGGACTTGAG ACGTTGATTC GAGATTTTGT TTTTCACAAG AAGACACCA ATATTTGGCC  4080
4081  CGTTGTTTAG TGAGCTTACT AGGCAATTAC TGGACAGTGT TGATTCGAGC AGATTTTTGT GTCTTGGAG CTGATATAT CAAAATACGA  4160
4161  GCGCAGATTG CGGATTTCTT CGGAGATCTC GACAGTCATG TGCCGATGGA TGTCTTGGAG GATTGGGTTT TGAAGACTTC TTGGGAGAAG  4240
4241  CAAATCTCAG AATGAATTCC ACTGTGCAGT AGAATACGAG ATCTGGCGAA GATTGGGTTT ATAAAAACTT GCATCTGGTA TCAAAGAAAG  4320
4321  TTTGGAAACA AGGGCATAGA AAGACCACCC TCAAGGATTA TACCGCCAGT TTGCTGCATG TTTGCCCTCG ATGCTTCCGA TGGAGAAAAT  4400
4401  AGCGGGGACG TCACGACGTT CATTGGAAAC ACTGTGTGCA TCTGCTGTAC TTTCAAAGG GTTGTGAGTT TACTTTTGCG CAACACTCCG  4480
4481  AATCAAAGGA GCCTTTTGCG GTGACGATAG TCTGCTGTAC TTTCAAAGG GTTGTGAGTT TACTTTTGCG CAACACTCCG  4560
4561  CGAATCTTAT GTGGAATTTT GAAGCAAAAC TGTTTAAAAA ACAGTATGGA TACTTTTGCG GAAGATATGT AATACATCAC  4640
4641  GACAGAGGAT GCATTGTGTA TTACGATCCC CTAAAGTTGA TCTCGAAACT TGGTGCTAAA CACATCAAGG ATGGGAACA  4720
```

FIG. 5-C

```
4721 CTTGGAGGAG TTCAGAAGGT GGTTCATAAG CTCTTTGTGA TGTTGCTGTT TCGTTGAACA ATTGTGCGTA TTACACACAG TTGGACGACG 4800
4801 CTGTATGGGA GGTTCATAAG ACCGCCCCTC CAGGTTCGTT TGTTTATAAA AGTCTGGTGA AGTATTTGTC TGATAAAGTT 4880
4881 CTTTTAGAA GTTTGTTTAT AGATGGCTCT AGTTGTTAAA GGAAAAGTGA ATATCAATGA GTTTATCGAC CTGACAAAAA 4960
4961 TGGAGCCGAT CTTACCGTCG ATGTTTACCC CTGTAAAGAG TGTTATGTGT TCCAAAGTTG ATAAAATAAT GGTTCATGAG 5040
5041 AATGAGTCAT TGTCAGAGGT GAACCTTCTT AAGGAGTTA AGCTTATTGA TAGTGGATAC GTCTGTTTAG CCGGTTTGGT 5120
5121 CGTCACGGGC GAGTGGAACT TGCCTGACAA TGCAGAGGA GGTGTGAGCG TGTGTCTGGT GGACAAAAGG ATGGAAAGAG 5200
5201 CCGAGGAGGC CACTCTCGGA TCTTACTACA CAGCAGCTGC AAAGAAAAGA TTTCAGTTCA AGGTCGTTCC CAATTATGCT 5280
5281 ATAACCACCC AGGACGCGAT GAAAAACGTC TGGCAAGTTT TAGTTAATAT AGAAATAATA TAAAATTAGG AAGATGTCAG CGGGTTTCTG 5360
5361 TCCGCTTTCT CTGGAGTTTG TGTCGGTGTG TATTGTTTAT CGTTGATGAG TTCATGGAAG TTTGAGAGAG AAGATTACAA 5440
5441 ACGTGAGAGA CGGAGGGCCC ATGGAACTTA CAGAAGAAGT TCCGCAAAGG GAAAAATAGT ATGTCCCTAT GTCGATCAGG 5520
5521 CTTGCAAAGT TTCGATCTCG AACCGGAAAA TTAAGGATTT AGTTTTTAAA ATCAATCATC CATCTCCGAA GTGTGTCTGC GGTCAGTGCC 5600
5601 GAACAAGAAC TATAGAAATG TTAAGGATTT TGGAGGAATG TACGCTCGAG ATCAATCATC GTCCTCCTTG GCCTCTCCTC AGCATGCAGG 5680
5681 CTACTGTCGC CGAATCGGAT CATGGTGAAC AAACACTTCT TGTCCCTTTC GGTCCTCATC GGAAGGAGAA TGGCGGGGTG GCCTCTCACTC TGATGGGCAA 5760
5761 TGCTGTCGTG GCTGTACGGT CTGAGCGAT CGCCGACATC GTCATCAACC ACCGCACGGC GGAGCACAAG TGATCTGCCG CAACTTGACA CAAGGCTACA 5840
5841 GCCGGGCAAG TCCAGGTGAT CGCCGACATC GTCATCAACC ACCGCACGGC GGAGCACAAG TGATCTGCCG CGACGACCCC TACGGCGATG 5920
5921 GGTGGACGAC CCCGGACACC GGCGGACGC CCGACTCCCG CCTCGACTGG GCCCCGCACA TGATCTGCCG CGACGACCCC TACGGCGATG CAAGGCTACA 6000
6001 TGCCTGGGCG GCTCGACTG GGCGGACGC CCGACTCCCG CCTCGACTGG GCCCCGCACA TGATCTGCCG CGACGACCCC TACGGCGATG GGCGTTCCAT 6080
6081 GGCAAGGGCG TCCAGGTGAT CGCCGACATC GTCATCAACC ACCGCACGGC GGAGCACAAG TGATCTGCCG CGACGACCCC TACGGCGATG GCATCTACTG 6160
6161 CCTCTTCGAG GCGGGACGC CCGGACACC GGGCGCGACT TCGCGCGCGC GGGCGCGACT CGCGCGCGC GACCACCTCA CAAGCGCGT CCAGCGGGAG 6240
6241 GCACCGGCAA CCCGGACACC GGCTCGACTG GCTCAAGATG GACATCGGCT TCGCGCGCGC GACCACCTCA CAAGCGCGT CCAGCGGGAG GCTACTCCGC 6320
6321 CTCATTGGCT GGCTCGACTG GCTCAAGATG GACATCGGCT CGAGCCGAGC TTCGCCGTGG CCGAGATATG GACGTCCATG GCAACGGCG 6400
6401 CGACATGGCA AAGATCTACA TCGACGCCAC CGAGCCGAGC TTCGCCGTGG CCGAGATATG GACGTCCATG GCAACGGCG 6480
6481 GGGACGGCAA GCCGAACTAC GACCAGAACG CGCACCGGCA AAGGGCATCC GGAGCTGGTC AACTGGGTCG GGCGCCAAC 6560
6561 AGCAACGGCA CGGCGTTCGA CTTCACCACC AAGGGCATCC TCAACGTCGC CGTGGAGGGC GAGCTGTGGC GCCTCCGCGG 6640
6641 CGAGGACGGC AAGGCGCCCG GCATGATCGG GTGGTGGCCG GCCAAGGCGA GCCAGGGCTAC CGACCTTCGT CGACAACCAC GACACCGGCT 6720
6721 CGACGCAGCA CCTGTGGCCG TTCCCCTCCG ACAAGGTCAT GCAAGGTCAT GCATACATCC TCACCCACCC CGGCAACCCA 6800
6801 TGCATCTTCT ACGACCATTT CTTCGATTGG GGTCTCAAGG AGGAGATCGA AGCGGATCTCT ACCTCGCGGA GCGCCTGGTG TCAATCAGAA ACCGGCAGGG 6880
6881 GATCCACCCG GCGAGCGAGC TGCGCATCAT GGAAGCTGAC AGCGGATCTCT ACCTCGCGGA GATCGATGGC AAGGTGATCA 6960
6961 CAAAGATTGG ACCAAGATAC GACGTCGAAC ACCTCATCCC CAGGGCTTC CAGGTCGTCG CGCACGGTGA TGGCTACGCA 7040
7041 ATCTGGGAGA AAATCTGACC taggctcgca aagtttcgaa ccaaatcctc aaaagaggt cgaaaaata ataataattt 7120
```

FIG. 5-D

```
7121 aggtaagggg cgttcaggcg gaaggcctaa accaaaaagt tttgatgaag ttgaaaaaga gtttgataat ttgattgaag 7200
7201 atgaagccga gacgtcggtc gcggattctg attcgtatta aatATGTCTT ACTCAATCAC TTCTCCATCG CAATTTGTGT 7280
7281 TTTTGTCATC TGTATGGGCT GACCCTATAG AATTGTTAAA CGTTTGTACA AATTCGTTAG GTAACCAGTT TCAAACACAG 7360
7361 CAAGCAAGAA CTACTGTTCA ACAGCAGTTC AGCGAGGTGT GGAAACCTTT CCCTCAGAGC ACGGTCAGAT TTCCTGGCGA 7440
7441 TGTTTATAAG GTGTACAGGT ACAATGCAGT TTTAGATCCT CTAATTACTG CGTTGCTGGG GGCTTTTGAT ACTAGGAATA 7520
7521 GAATAATCGA AGTAGAAAAC CAGCAGAGTC CGACAACAGC TGAAACGTTA GATGCTACCC GCAGGGTAGA CGACGCTACG 7600
7601 GTTGCAATTC GGTCTGCTAT AATAATTTA GTTAATGAAC TAGTAAGAGG TACTGGACTG TACAATCAGA ATACTTTTGA 7680
7681 AAGTATGTCT GGGTTGGTCT GGACCTCTGC ACCTGCATCT TAAATGCATA ggtgctgaaa tataagttt gtgttttctaa 7760
7761 aacacacgtg gtacgtacga tgttttttccc tggacttaaa tcgaaggta gtgtcttgga gcgcgcggag 7840
7841 taaacatata tggttcatat atgtccgtag gcacgtaaaa aaagcgaggg attcgaattc ccccggaacc cccggttggg 7920
7921 gcccaG                                                                               7926
         |        |        |        |        |        |        |        |
         10       20       30       40       50       60       70       80
```

METHOD FOR RECOVERING PROTEINS FROM THE INTERSTITIAL FLUID OF PLANT TISSUES

This application is a continuation of U.S. patent application Ser. No. 10/119,330 filed Apr. 8, 2002, now U.S. Pat. No. 6,617,435, which is a continuation of application Ser. No. 09/726,648, filed Nov. 28, 2000, now U.S. Pat. No. 6,441,147; which is a continuation of application Ser. No. 09/500,554, filed Feb. 9, 2000, now U.S. Pat. No. 6,284,875; which is a continuation of U.S. application Ser. No. 09/132,989, filed Aug. 11, 1998, now abandoned.

FIELD OF THE INVENTION

The present invention relates generally to the field of protein production and purification. More specifically, the present invention relates to a method for isolating commercial scale quantities of highly concentrated, active proteins from the intercellular material of plants via a vacuum and centrifugation process which does not destroy the plant material, permitting secondary protein extraction from the plant material.

BACKGROUND OF THE INVENTION

There are many examples of valuable proteins that are useful in pharmaceutical and industrial applications. Often these molecules are required in large quantities and in partially or highly purified formulations to maintain product quality and performance. Plants are an inexpensive source of proteins, including recombinant proteins. Many have proposed the desirability of producing proteins in large amounts in plants. However, the problems associated with extracting and processing products from homogenized plant tissues as well as purifying and recovering the recombinant protein product have been recognized as substantial. Austin et al. *Annals New York Academy of Science*, 721:234–244 (1994). These problems represent major impediments to successful recombinant protein production in plants on a large and commercially valuable scale.

Plant cells are thought to synthesize proteins on the membranes of the endoplasmic reticulum and transport the proteins synthesized to the cell surface in secretory vesicles formed at the Golgi apparatus. A discussion of the topic is provided by Jones et al., *New Phytology*, 111:567–597 (1989). Significant research has been devoted to elucidating the specific mechanisms related to protein secretion for several particular proteins in specific plant tissues or cell cultures. Examples of such efforts are presented by Herbers et al., *Biotechnology* 13:63–66 (1995), Denecke et al., *The Plant Cell* 2:51–59 (1990), Melchers et al., *Plant Molecular Biology* 21:583–593 (1993) and Sato et al., *Biochemical and Biophysical Research Communications* 211(3):909–913 (1995). In the case of proteins not secreted into the plant cell apoplasm or intercellular space, a mechanism for lysing the plant cell wall must be utilized in order to release and capture the protein of interest. Plant cells must be exposed to very high shear forces in order to break the cell walls and lyse cellular membranes to release intracellular contents. Proteins of interest, whether recombinantly produced or naturally produced by the subject plant, are thereby exposed to a hostile chemical environment and are particularly subject to oxidative and proteolytic damage due to the exposure of the product to enzymes and small molecules that were compartmentalized before homogenization of the tissue. In addition, most of the other total cellular protein is mixed with the protein of interest creating formidable purification problems if such a cell lysis procedure is performed. In order to use the biosynthetic capacity of plants for reliable protein production, a process to obtain specific proteins that can be secreted into the intercellular space (apoplasm) of plant tissues is desirable. Such a procedure would forego the need for homogenization. If such a procedure is performed, the fraction of plant material containing one or more proteins of interest might be obtained without homogenization. Therefore, such a procedure provides that the plant extract is enriched for the particular protein of interest, and the protein is protected from some chemical and enzymatic degradation.

Since the valuable proteins and products of interest are partitioned or secreted into the interstitial spaces, vacuum pressure facilitates the introduction of infiltration medium into the interstitial space. Similarly, various forces can be applied to remove the retained fluid. Centrifugal force of 1,000×G is effective. Using gravity, the retained fluid can be collected in a trap under vacuum. With or without vacuum infiltration of a buffer, the enzyme can be recovered by freezing the tissue, thawing and applying a physical press to recover the fluid. However, such a procedure results in an undesirable increased cellular lysis.

Genetically modified plants are a reliable source for the production of recombinant proteins. Because the biological product is accumulated under nonsterile growth conditions and the production may be scaled to the quantities desired in a relatively inexpensive manner, it is feasible to exploit a dilute but enriched source such as the interstitial fluid fraction as a source for harvesting proteins of interest on an industrial scale. A variety of proteins of interest may be harvested from recombinant plant sources, however, highly active, pharmaceutical quality enzymes, cytokines and antibodies are particularly valuable products that can be developed by this process.

SUMMARY OF THE INVENTION

The present invention features a method for extracting highly concentrated, active proteins from the intercellular space of plants. The intercellular space consists of a matrix of fluid, protein and cell wall carbohydrates. The method is applicable to the large, commercial-scale isolation of proteins desired from plant cells whether such proteins are naturally occurring or are produced by recombinant technology. The vacuum and centrifugation process, as explained below, allows extraction of protein from the interstitial fluid of the plant without destroying the plant material, permitting further extraction of desired protein from the plant material.

In a broad aspect, the method comprises infiltrating plant leaves with a buffer solution by subjecting submerged plant foliage to a substantially vacuum environment, removing the excess liquid from the plant foliage after exposing the foliage to the substantially vacuum environment, and centrifuging the foliage to obtain the interstitial fluid. As a result of such a procedure, large amounts of desirable proteins may be removed from the intercellular space of plants thereby making it feasible to isolate naturally-occurring proteins from plant foliage and making it possible to produce recombinantly the desired proteins in plants and recover the same in commercially valuable quantities without homogenizing the plant foliage or otherwise significantly lysing the plant cells themselves. This material is referred to as an interstitial fluid, hereinafter "IF", IF extract.

In one embodiment, the subject plant leaves are disected completely or substantially down the midrib (substantially in halves) before exposing them to the buffer solution. In another preferred embodiment, the leaves and buffer solution are subjected to a vacuum pressure of about 200 up to 760 mm Hg. Even more preferably, the leaves and buffer solution are subjected to a vacuum pressure of about 400 up to 760 mm Hg. And most optimally, the leaves and buffer solution are subjected to a vacuum pressure of up to about 760 mm Hg. In yet other preferred embodiments, the leaves are subjected to a low speed centrifugation having a G-force range of about 50 to 5,000×G or less after the excess buffer solution is removed. Most preferably, the leaves are subjected to centrifugation having a G-force of about 2,000×G.

BRIEF DESCRIPTION OF THE FIGURES

FIG. 5 Viral cDNA Sequence of Plasmid TT01A 103L

DETAILED DESCRIPTION OF THE INVENTION

Figure 1:
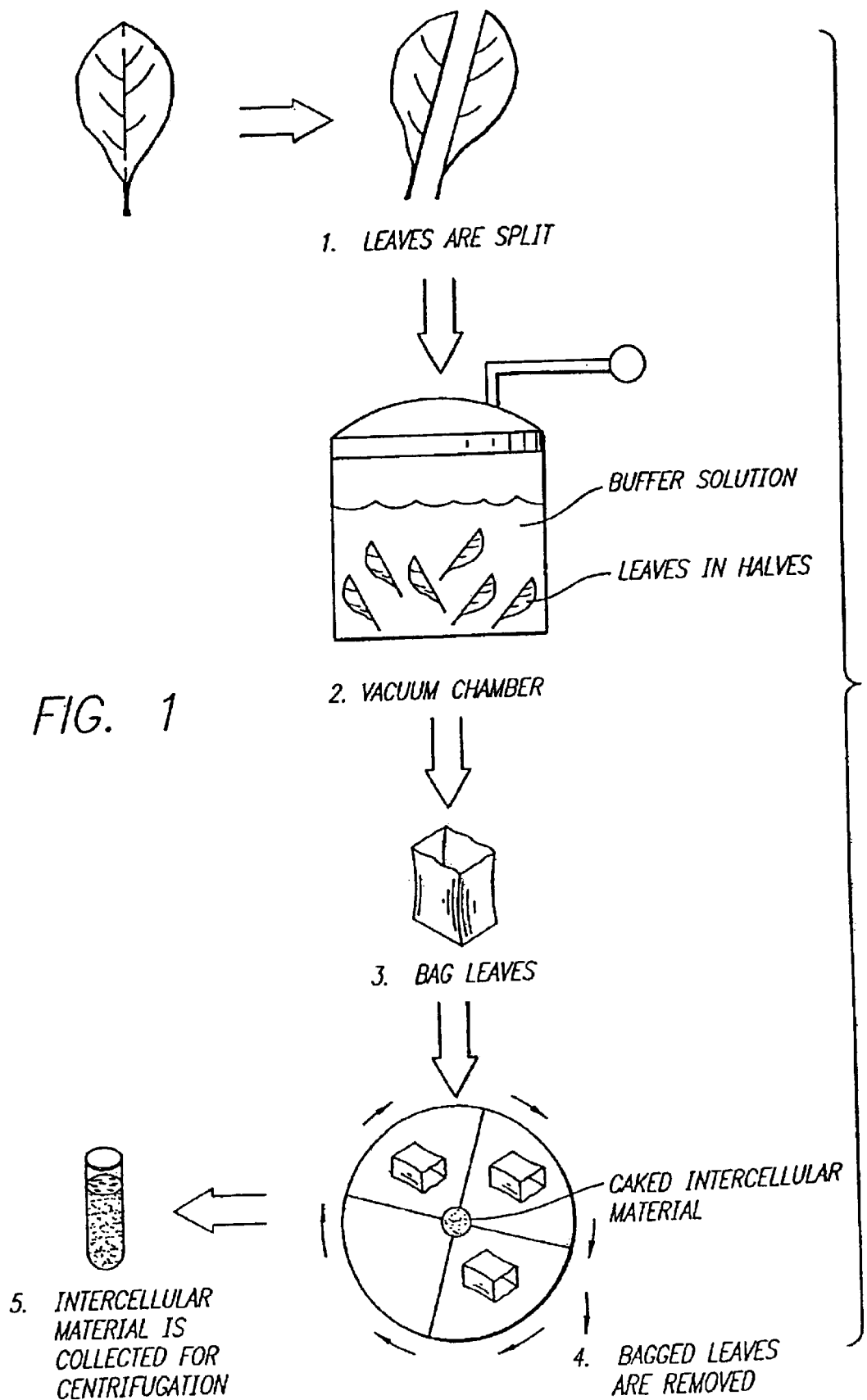
FIG. 1 General Overview Of The IF Extraction Process

The present invention features a method for extracting proteins from the intercellular space of plants. The method is applicable to the large-scale commercial isolation of highly concentrated and active proteins desired from plant cells whether such proteins are naturally occurring or are produced by recombinant technology, including the use of plant viral vectors or the use of transgenic plants. The vacuum and centrifugation process of the present invention permits extraction of protein from the intercellular space without destroying the plant material, thereby permitting further secondary extraction of desired proteins from the plant material. These proteins derived from the secondary extraction process can be either the same or different as those proteins purified from the IF fluid.

The method generally comprises the steps of infiltrating plant foliage with a buffer solution by subjecting the submerged plant foliage to a substantially vacuum environment, removing the excess liquid from the plant foliage after exposing the foliage to the substantially vacuum environment, and centrifuging the foliage. As a result of such procedure, large amounts of desirable proteins may be removed from the intercellular space of plants thereby making it feasible to isolate both naturally-occurring and recombinantly produced proteins from plant foliage in commercial-scale quantities without homogenizing the plant cells, allowing secondary extraction of desired protein from the plant cell material.

Work has been conducted in the area of developing suitable vectors for expressing foreign DNA in plant hosts. Ahlquist, U.S. Pat. No. 4,885,248 and 5,173,410 describes preliminary work done in devising transfer vectors which might be useful in transferring foreign genetic material into a plant host for the purpose of expression therein. Additional aspects of hybrid RNA viruses and RNA transformation vectors are described by Ahlquist et al. in U.S. Pat. Nos. 5,466,788, 5,602242, 5,627,060 and 5,500,360 all of which are herein incorporated by reference. Donson et al., U.S. Pat. Nos. 5,316,931 and 5,589,367, herein incorporated by reference, demonstrate for the first time plant viral vectors suitable for the systemic expression of foreign genetic material in plants. Donson et al. describe plant viral vectors having heterologous subgenomic promoters for the stable systemic expression of foreign genes. Hence, the use of plants to produce recombinant proteins on a commercial scale is now possible. The present application solves the problem of extracting these proteins of interest from the interstitial fluid of plant foliage.

Protein secretion in plants is a fundamental yet not fully understood process. It is known that secreted proteins are synthesized on the membranes of the rough endoplasmic reticulum and transported to the cell surface by secretory vesicles formed on the Golgi apparatus. Moreover, it is known that a signal peptide is required for translocation of the secreted proteins across the endoplasmic reticulum. Proteins which are transported into the lumen of the endoplasmic reticulum may then be secreted into the interstitial space provided they are not sorted by the cell to another compartment such as the vacuole. As knowledge about this process increases, it may be possible to design recombinant proteins which are specifically intended for secretion into the interstitial space of plant cells in which they are produced.

If a significant percentage (approximately 10% or greater) of the total product is secreted then it may be preferable to isolate proteins of interest from the intercellular space of plants. Otherwise, a mechanism for lysing the plant cell wall must be utilized in order to release and capture the protein of interest. Plant cells must be exposed to very high shear forces in order to break the cell walls and lyse cellular membranes to release intracellular contents. Proteins of interest, whether recombinantly produced or naturally produced by the subject plant, are thereby exposed to a hostile chemical environment and are particularly subject to oxidative and proteolytic damage that is often enzymatically catalyzed. In addition, most of the other total cellular protein is mixed with the protein of interest creating formidable purification problems if such a cell lysis procedure is performed.

Intercellular fluid extracts have previously been prepared from vacuum infiltrated foliage for a variety of experimental purposes. These extracts are comprised of proteins, both native and nonnative, as well as other molecules. In Klement, Z. (1965) *Phytopathological Notes*:1033–1034, the growth promoting properties of the extract were documented using a plant pathogenic bacterial species. Using marker enzymes for the IF and cytosolic compartments of the plant leaf cell, Rathmell and Sequera (1974), *Plant Physiol*. 53:317–318 confirmed the enrichment of a specifically secreted protein fraction and noted the utility of these extracts in basic research studies pertaining to biochemical and physiological investigations. Parent and Asselin (1984) *Can. J. Bot*. 62:564–569, characterized a number of proteins that were induced by pathogen stress and secreted in the IF (pathogenesis-related or PR proteins) and the method was applied to localize enzymatic activities and proteins to subcellular compartments. Van den Blucke et. al. (1989) *PNAS* 86:2673–2677; Heitz et al. (1991) *Plant Physiol*. 97:651–656. Regalado and Ricardo (1996) *Plant Physiol*. 110:227–232 noted that specific IF proteins appear to be constitutively expressed.

Depending on the buffer composition and treatment, there may be various additional components in IF extracts including, for example, components originating from the rough and smooth endoplasmic reticulum, the golgi apparatus, the nucleus, the vacuole, the plasma transmembrane, the cytosol, the mitochondria, the chloroplasts, peroxisomes, any associated membranes and organelles.

In genetically modified plants, IF extraction methods as well as other methods have been used to demonstrate the subcellular localization of a portion of the recombinant product. Sijomns et al. (1990) *Bio/Technology* 8:217–221; Firek et al. (1993) *Plant Molecular Biology* 23:861–870; Voss et al. (1995) *Molecular Breeding* 1:39–50; De Wilde etal. (1996) *Plant Science* 114:233–241. IF extracts have been used as a starting material to purify small quantities of plant or plant pathogen-derived proteins for biochemical characterization. Melchers et al. (1993) *Plant Molecular Biology* 21:583–593; Sato et al. (1995) *BBRC* 211:909–913; Kinai et al. (1995) *Plant Cell* 7:677–688; Liu et al. (1996) *Plant Science* 121:123–131; Maggio et al. (1996) *Plant Molecular Biology Reporter* 14:249–259.

Therefore, there is a need to isolate an extracted material having a higher specific activity of the active material (U activity/mg protein) and, therefore, this provides an enrichment process of IF components at commercial scale.

It is not appreciated in the prior art that IF extracts might be generally useful as starting material for the large scale purification of highly active and potent biochemicals that may, for example, have applications as a source of human therapeutics. Often other methods of purification are pursued even when the product is shown to be secreted (Herbers et al. 1995, supra). The failure to develop the IF method as a commercially feasible source of recombinant protein products is due to a combination of the following factors: 1) an incomplete characterization of the extracts, i.e. a determination of what percent of the total recombinant protein can be obtained by IF methods at what level of enrichment, 2) failure by others to demonstrate suitable activity of a product in a highly purified form and 3) a lack of description of industrial-scale equipment to process reasonable quantities of biomass for this purpose.

The present invention involves a vacuum and centrifugation process to provide for commercial-scale protein extraction from plants. As a result of the present invention, large amounts of active proteins of interest may be removed from the intercellular space of plants and concentrated for further purification thereby making it feasible to isolate naturally-occurring and recombinantly-produced proteins from plant foliage in commercially valuable quantities. This process has an additional advantage in that the resulting plant tissue following IF extraction is not destroyed and may be used for recovery of other valuable components by other means.

The foliage may be harvested in any manner that is convenient. In a preferred embodiment, the subject plant leaves are removed from the plant and are dissected completely or substantially lengthwise parallel to the midvein substantially in halves before exposing them to a buffer solution such that the ends of numerous large lateral veins are exposed.

Once the leaves are cut, they may be exposed to a buffer solution. A routine EDTA or Tris buffer solution is suitable, though those skilled in the art will appreciate that any buffer may be more or less appropriate for a given plant or protein of interest. In some instances, water may be acceptable or even preferred as a solution. It is not contemplated that the nature of the buffer solution, specific pH or temperature are crucial to the embodiments within the scope of the invention. However, it is generally recommended to maintain conditions which avoid oxidation, precipitation, proteolysis or denaturation of the one or more proteins of interest. Thus, pH, temperature, and other such variables should be monitored and altered as needed.

Once the leaves of the plant have been placed in a buffer solution, they are subjected to a substantially vacuum environment. It is believed that vacuum pressure expedites soaking of the buffer solution by the leaf. In some embodiments, the vacuum pressure may be about 200 to 760 mm Hg. Most preferably, the leaves and buffer solution are subjected to a vacuum pressure of about 400 to 760 mm Hg. The amount of vacuum pressure may be varied within the scope of the invention. Also, the duration may be varied within the scope of the invention, however, exposure to a vacuum environment for durations of around a few seconds to 10 minutes has proven especially effective. In some embodiments of the invention, the leaves in buffer solution are exposed to a vacuum environment repeatedly. It is believed that one to three separate exposures may be especially effective. However, the number of exposures, duration of exposure and amount of force of the vacuum may be adjusted according to the preferences of the practitioner and to capture the most efficient embodiments of the method as it applies to specific plants and proteins of interest. Additionally, one skilled in the art can invision that molecules or products of interest other than peptides and proteins could be recovered from the interstitial fluid using methods generally described in the instant invention. For example, the methods described in the instant invention can be used to recover lipids, carbohydrates, lipoproteins, sugars, polysaccharides, fatty acids, nucleic acids and polynucleotides.

The plant tissue is then removed from the buffering solution. They may or may not be subjected to a desiccation step to remove the buffer as the need or desire dictates. The leaves may then be placed in any convenient geometric array for centrifugation. In preferred embodiments the leaves are transferred from the centrifuge by means of a discontinuous discharge basket centrifuge rotor. When a discontinuous discharge basket centrifuge rotor is used, an initial spin is performed to move the biomass to the wall of the rotor and then the full-speed spin is performed. In especially preferred embodiments, it is contemplated that a large volume of leaves will be simultaneously subjected to the vacuum and centrifuging devices. Thus, it is anticipated that large, commercially available vacuum pumps and basket centrifuges such as those made by Heine®, Ketna® or Sandborn® will be used in the subject method. It is especially preferred to assemble the leaves in bags for a basket centrifuge.

The leaves may then be subjected to centrifugation after the excess buffer solution is substantially removed. In preferred embodiments, it is contemplated that low speed centrifugation is appropriate. By low speed centrifugation is meant about 5,000×G or less. By the centrifugation procedure, the interstitial fluid is removed from the plant. The interstitial fluid may be collected in any convenient collecting device, e.g., a tank, or directed to additional purification equipment, e.g., chromatography and ultrafiltration.

Once the interstitial fluid is collected from plant leaves, the one or more proteins of interest may be concentrated and purified according to any suitable purification procedures. Such procedures may include but are not limited to protein precipitation, expanded bed chromatography, ultrafiltration, anion exchange chromatography, cation exchange chromatography, hydrophobic-interaction chromatography, HPLC, FPLC and affinity chromatography. A general discussion of some protein purification techniques is provided by Jervis et al., *Journal of Biotechnology* 11:161–198 (1989), the teachings of which are herein incorporated by reference.

It is contemplated that the method of the present invention is useful with any and all plant tissues (such as leaves, roots, shoots, stems, flowers, fruits, embryos, seedlings) that may be treated as saturated solids after vacuum infiltration. For example, this may include germinating embryos and seedlings. However, plants possessing substantially symmetrical leaves with a midrib may be especially useful in the present method because the interstitial fluid may be more easily obtained from such leaves as a result of the highly suitable morphology. In especially preferred embodiments, the plant used is tobacco since tobacco has proven to be especially useful in producing recombinant proteins of interest on a large scale. However, it is not intended that the present invention be limited to any particular plant species or tissues.

The following definitions are provided merely to clarify the present invention:

By "vacuum environment" is meant any environment regardless of the confines defining the same and regardless to the mechanism producing the same in which the atmospheric pressure has been substantially reduced from that observed under normal conditions at sea level.

By "protein of interest" is meant any complete protein or peptide or fragment thereof whether naturally occurring in a cell or produced therein by recombinant methods. The term is intended to encompass amino acid sequences which are glycosylated as well as those which are not glycosylated. The term is also intended to encompass sequences which are naturally occurring or wild type and those which have been modified or mutated, including modification to include a signaling peptide sequence which causes the protein to be directed to a specific compartment within the cell. The term is also intended to encompass protein fusions.

By "interstitial fluid" is meant the extract obtained from all of the area of a plant not encompassed by the plasmalemma i.e., the cell surface membrane. The term is meant to include all of the fluid, materials, area or space of a plant which is not intracellular (wherein intracellular is defined to be synonymous with innercellular) including molecules that may be released from the plasmalemma by this treatment without significant cell lysis. Synonyms for this term might be exoplasm or apoplasm or intercellular fluid or extracellular fluid. Interstitial fluid is abbreviated in the instant invention as IF.

EXAMPLES

The following examples further illustrate the present invention. These examples are intended merely to be illustrative of the present invention and are not to be construed as being limited.

for the isolation of highly active products on a very large scale. Those skilled in the art may optimize the process for numerous variables specific for each protein such as buffer composition and temperature, etc.

Example 1
Extraction of α-Trichosanthin Protein

α-Trichosanthin (α-TCS) is a eukaryote ribosome-inactivating enzyme that cleaves an N-glycosidic bond in 28S rRNA. α-TCS, as well as other ribosome-inactivating proteins and conjugates are being evaluated as therapeutics for cell-directed death. In previous work we demonstrated that plants transfected with a proprietary RNA viral vector produce recombinant α-TCS to 2% of the total soluble leaf protein with high fidelity (Kumagai et al. *PNAS* 90:427–430 (1993)).

Leaves from plants transfected with the vector TB2 (ATCC Deposit No. 75280) were removed at the petiole and slit down the midrib into two equal halves. To obtain a total cellular homogenate, one group of half-leaves was ground in the presence of 4 volumes of detergent extraction buffer (100 mM potassium phosphate pH 6.5 mM EDTA, 10 mM, α-mercaptoethanol and 0.5% w/v sodium taurocholate) with a mortar and pestle after freezing the tissue in liquid nitrogen. To recover the interstitial fluid (IF), the same enzyme extraction buffer was infiltrated into the opposing group of half-leaves by submerging the tissue and pumping a moderate vacuum (500 mm Hg). After draining off excess buffer, the undisrupted half-leaves were rolled gently in parafilm, placed in disposable tubes and the interstitial fluid (IF) was collected by low-speed centrifugation (1,000×G) for a period of 5–15 minutes. The weight of buffer recovered from the infiltrated leaf tissue is recorded and varies from approximately one-half to equal the original weight of the leaf. α-TCS expression in IF extracts was confirmed by Western analysis and levels were quantified using a densitometer tracing of a Coomassie-stained gel. Total protein was determined by the method described by Bradford. Bradford, *Anal. Biochem* 72:248 1976.

The following data presented as Table 1 demonstrate that recombinant α-TCS, shown in previous work to retain full enzymatic activity, may be successfully extracted from the interstitial fluid of plant leaves using the present method. The IF method results in a recovery of 9% of the total α-TCS of the leaf at a 6-fold enrichment relative to an extract obtained by homogenization (H). The α-TCS production results may be improved by optimizing the time post-inoculation with the viral vector and minimizing the contamination of viral coat protein in the interstitial fraction.

TABLE 1

| Sample | Fresh Weight (gr) | Total Volume (ml) | Protein Conc. (mg/ml) | Total Protein (mg) | Protein Yield (mg/gr) | Rprotein Conc. (mg/ml) | Total RProtein (mg) | 1Rprotein Yield (mg/gr) | % Recovery RProtein In IF | X-Fold Purification |
|---|---|---|---|---|---|---|---|---|---|---|
| TB2/IF | 8.00 | 7.8 | 0.13 | 1.03 | 0.13 | ND | ND | ND | ND | ND |
| TB2/TCS/IF | 8.00 | 8.3 | 0.14 | 1.20 | 0.15 | 0.017 | 0.143 | 0.018 | 9 | 6 |
| *TB2/TCS/H | ND | ND | ND | 80.00 | ND | ND | 1.600 | ND | ND | ND |

Figure 4:
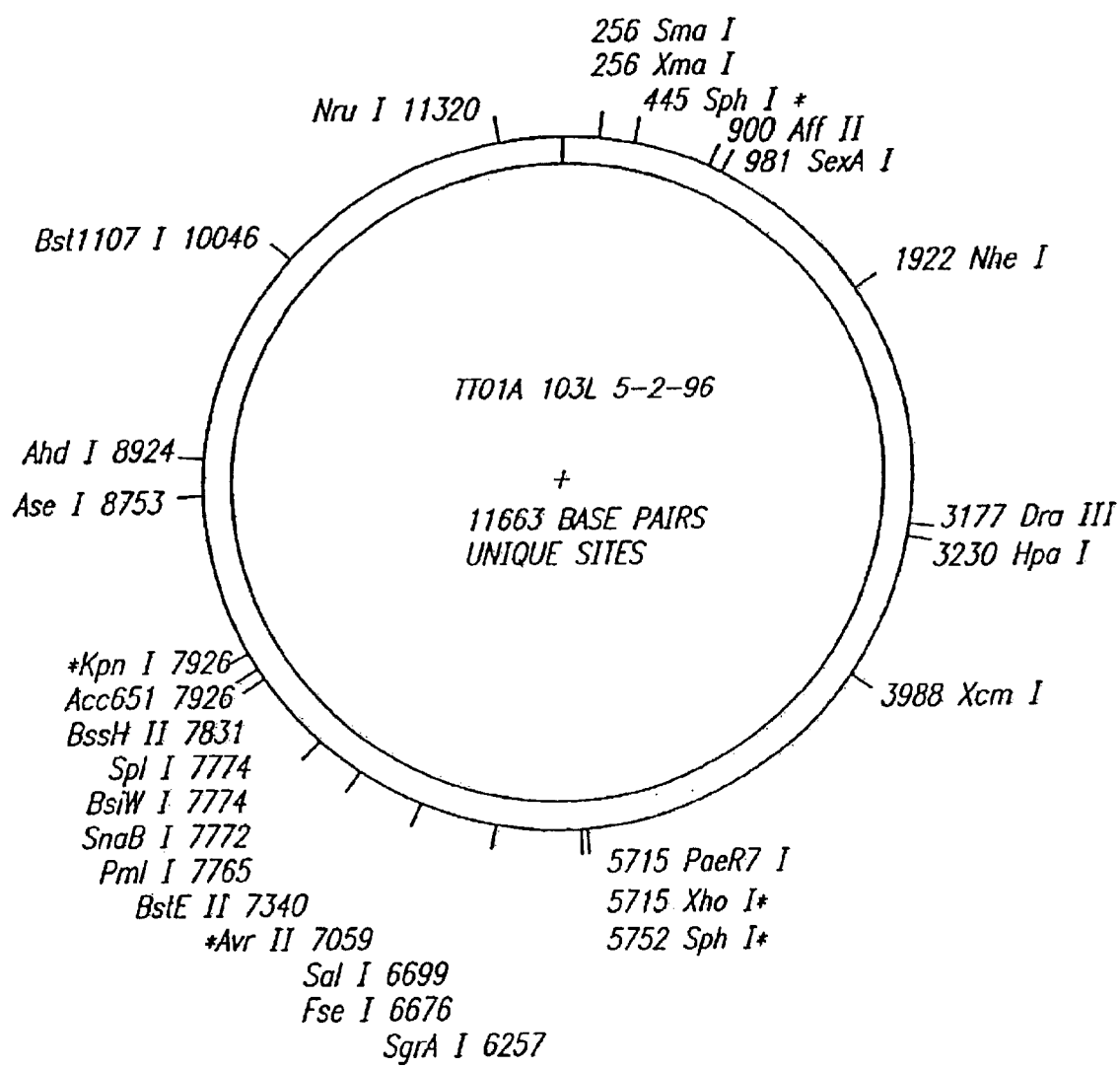
FIG. 4 Plasmid map of TT01A 103L (SEQ ID NO: 1)

*Calculated from PNAS 90:427–430 (1993)
IF = interstitial fluid extraction
H = homogenization extraction
ND = Not determined These experiments demonstrate that a significant portion of the total protein in the leaf can be simply recovered from the interstitial fraction while enriching for purity. These experiments further demonstrate that the methods are useful Example 2
Extraction of Amylase Protein Amylase (AMY) is an important industrial enzyme used to degrade starch. Leaves from plants transfected with the vector TT01A 103L were removed at the petiole and slit down the midrib into two equal halves. The plasmid map of TT01A 103L is shown in FIG. 4. The viral cDNA sequence of plasmid TT01A 103L is shown in FIG. 5. To obtain a total cellular homogenate, one group of half-leaves was ground in the presence of 4 volumes of detergent extraction buffer (100 mM potassium phosphate pH6.5, 5 mM EDTA, 10 mM, α-mercaptoethanol and 0.5% w/v sodium taurocholate) with a mortar and pestle after freezing the tissue in liquid nitrogen. To recover the interstitial fluid (IF), the same enzyme extraction buffer was infiltrated into the opposing group of half-leaves by submerging the tissue and pumping a moderate vacuum (500 mm Hg). After draining off excess buffer, the undisrupted half-leaves were rolled gently in parafilm, placed in disposable tubes and the interstitial fluid (IF) was collected by low-speed centrifugation (1,000×G for about 15 minutes). The weight of buffer recovered from the infiltrated leaf tissue is recorded and varies from approximately one-half to equal the original weight of the leaf. AMY expression in IF extracts was quantified using a commercially available enzyme assay reagents and protocol. Total protein was determined by the method described in Bradford, *Anal. Biochem* 72:248 1976. The AMY enzyme assay is described in Sigma Procedure No. 577.

The following data presented as Table 2 demonstrate that active recombinant AMY may be successfully extracted human glucocerebrosidase. Specificity of the plant-expressed recombinant enzyme was confirmed by hydrolysis of 14C-radiolabeled glucosylceramide. According to these expression results the rGCB positive transformants were ranked into moderate (A), low (B) and negligible (C) activity groups.

We also found reaction conditions to preferentially inhibit rGCB enzyme activity in the presence of plant glucosidases using the suicide substrate conduritol B-epoxide (CBE). Total glucosidase activity, and rGCB activity were measured by hydrolysis of the fluorescent substrate 4-methylumbelliferyl glucopyranoside (4-MUG) with and without CBE. Leaves from transgenic plants were removed at the petiole and disected down the midrib into two equal halves to make a convenient size leaf material for the equipment used. To obtain a total cellular homogenate, one group of half-leaves was ground in the presence of 4 volumes of detergent extraction buffer (100 mM potassium phosphate pH 6.5 mM EDTA, 10 mM, α-mercaptoethanol and 0.5% w/v sodium taurocholate) with a mortar and pestle after freezing the tissue in liquid nitrogen. One of ordinary skill in the art could readily envision a buffer wherein the EDTA is substituted with other chelaters such as EGTA and citrate. One of ordinary skill in the art could readily envision a buffer solution wherein α-mercapto ethanol

TABLE 2

| Sample | Fresh Weight (gr) | Total Volume (ml) | Protein Conc. (mg/ml) | Total Protein (mg) | Protein Yield (mg/gr) | Rprotein Conc. (Uml) | Total RProtein (U) | 2Specific Yield (U/gr) | 3RProtein Yield (U/gr) | % Recovery RProtein In IF | X-Fold Purification |
|---|---|---|---|---|---|---|---|---|---|---|---|
| Amylase/IF | 1.76 | 1.8 | 0.22 | 0.39 | 0.22 | 0.319 | 0.57 | 0.33 | 1.463 | 34 | 27 |
| Amylase/H | 1.76 | 5.8 | 5.40 | 31.33 | 17.80 | 0.290 | 1.68 | 0.96 | 0.054 | ND | 1 |

IF = Interstitial fluid extraction
H = homogenization extraction
ND = Not determined from the interstitial fluid of plant leaves using the present method. The IF method results in a recovery of 34% of the total AMY activity of the leaf at a 27-fold enrichment relative to an extract obtained by homogenization (H). The AMY production results may be improved by optimizing the time post-inoculation with the viral vector and minimizing the contaminating viral coat protein from the intercellular fraction.

Example 3
Extraction of Glucocerebrosidase Protein

Glucocerebrosidase (GCB), either derived from human placental tissue or a recombinant form from Chinese hamster ovary cells (CHO), is presently used in an effective but costly treatment of the heritable metabolic storage disorder known as Gaucher disease. We combined a dual promoter from Cauliflower Mosaic Virus (35S), a translational enhancer from Tobacco Etch Virus and a polyadenylation region from the nopaline synthetase gene of *Agrobacterium tumefaciens* with the native human GCB cDNA to create plasmid pBSG638. These expression elements are widely used to provide the highest possible constitutive expression of nuclear-encoded genes in plants.

Using a standard *Agrobacterium*-mediated transformation method, we regenerated 93 independent kanamycin-resistant transformants from leaf discs of four different tobacco cultivars (the TO generation). In Western blots of total protein extracts, cross-reacting antigen was detected in 46 of these TO individuals with antibody raised against is substituted by other antioxidants including ascorbate, sodium metabisulfite and dithiothreitol. One of ordinary skill in the art can readily invision that a buffer solution could substitute the sodium taurocholate with other detergents including: SDS, Triton® (t-octylphenoxypolyethoxyethanol), Tween® (fatty acid esters of polyoxyethylene sorbitan), phospholipids, bile salts, sodium deoxycholate and sodium lauryl sulfate. To recover the interstitial fluid (IF), the same enzyme extraction buffer was infiltrated into the opposing of group of half-leaves by submerging the tissue and pumping a moderate vacuum (500 mm Hg). After draining off excess buffer, the undisrupted half-leaves were rolled gently in parafilm, placed in disposable tubes and the interstitial fluid (IF) was collected by low-speed centrifugation (1,000×G) for about 15 minutes. The weight of buffer recovered from the infiltrated leaf tissue is recorded and varies from approximately one-half to equal the original weight of the leaf. Using the suicide substrate, conduritol β-epoxide (CBE), inhibition of recombinant glucocerebrosidase (rGCB) activity in the presence of plant glucosidases was achieved. Enzyme activity was measured at 37° C. in a reaction mixture containing 5 mM methylumbelliferyl β-D glucoside, 0.1 M potassium phosphate, 0.15% Triton-X100, 0.125% sodium taurocholate, 0.1% bovine serum albumin, pH 5.9 with and without CBE. Total glucosidase activity and rGCB activity were measured by hydrolysis of the fluorescent substrate 4-methylumbelliferyl glucopyranoside. One unit of activity is defined as the amount of enzyme required to catalyze the hydrolysis of 1 nmol of substrate per hour. Total protein was determined using the Bio-Rad Protein Assay® based on the method of Bradford (Bradford, M., *Anal. Biochem.* 72:248; 1976)

The following data presented as Table 3 demonstrate that active recombinant GCB may be successfully extracted from the interstitial fluid of plant leaves using the present method. The IF method results in a recovery of 22% of the total GCB activity of the leaf at a 18-fold enrichment relative to an extract obtained by homogenization.

Example 4
Extraction of Avian Interferon Type II (Gamma)

Avian (chicken) interferon type II (gamma) has been expressed and active enzyme extracted from the interstitial space of *Nicotiana benthamiana* and *Nicotiana tabacum*. The interferon could be efficiently extracted from plants grown in the field or greenhouse using either gram (bench-scale extraction) or Kg (pilot-scale extraction) quantities of plant tissue.

Actively growing *N. benthamiana* or *N. tabacum* were inoculated with either infectious transcripts or virion of a recombinant plant construct as described by Donson et al., supra, harboring the chicken interferon gamma gene. Avian interferon was extracted from systemically infected leaves 10 days to 3 weeks post inoculation.

Example 4a

For bench-scale extractions, systemically infected leaves (3–80 grams) were detached from the plant at the leaf base, weighed, and placed in an appropriate sized beaker. The leaf material was completely covered with a buffered solution (100 mM Tris-HCl pH 7.5 buffer containing 5 mM $MgCl_2$ and 2 mM EDTA). The immersed leaves were covered with a Nalgene vacuum jar and a vacuum was pumped (720 mm Hg) and held for 2 minutes and then rapidly released. This vacuum infiltration was then repeated for a total of two cycles. Following the vacuum infiltrations, the leaves were removed from the beaker and surface buffer was removed from the leaves surface by blotting between absorbent paper. Leaves were placed in a 250 ml bottle, containing a supported mesh which allows for the separation and recovery of the IF from the leaf material. The interstitial fluid (IF) was recovered from the vacuum infiltrated leaves by centrifugation (3,000×G, 15 minutes).

Example 4b

For pilot-scale extractions, systemically infected leaves from field grown plants were stripped off the stalks by hand and weighed. Five kg of leaves were placed into polyester mesh bags (Filtra-Spec®, 12–2–1053), and two×5 kg bags of leaves were placed into a metal basket.

The metal basket containing the leaf material was placed in a 200 L Mueller® vacuum tank containing ~50 liters of buffered solution (100 mM Tris-HCl pH 7.5 buffer containing 5 mM $MgCl_2$ and 2 mM EDTA). A 70 lb. stainless steel plate was placed over the leaves/bags to assure complete immersion. A vacuum was pumped to 27 inches Hg and held for 1 minute and then rapidly released. This vacuum infiltration was then repeated for a total of two cycles. Following the vacuum infiltrations, the leaves and basket were removed from the vacuum tank. The bags containing the vacuum infiltrated leaves were allowed to gravity drain surface buffer for ~10 minutes, prior to centifugation. The interstitial fluid (IF) was recovered from the vacuum infiltrated leaves by centrifugation (1,800×G, 30 minutes) using a Heine® basket centrifuge (bowl dimensions, 28.0 inch diameter×16.5 inches). Collected IF was filtered through a 25 μm, Rosedale® sock filter and then through a 5 μm, Campbell Waterfilter® cartridge filter and then stored at 4° C., prior to analysis.

The amount of interferon protein in an IF extract was determined by quantitative imrnmunoblotting procedures using specific antisera to avian type II interferon and *E. coli* produced type II interferon in known quantities as standard. Based on quantitative immunoblotting, and partial purification, we estimate the specific activity of interferon in *N. benthamiana* IF at or near $10^7$ U/mg which is essentially equal to interferon isolated from native sources. Biological activity was determined by the nitrous oxide (NO) release assay as described in Lowenthal, J. W., Digby, M. R. and York, J. J. Production of Interferon-y by Chicken T Cells, *J. Interferon and Cytokine Res.* (1995) 15:933–938. Specificity of activity was determined by pre-incubation of IF fluid with a neutralizing antibody followed by measuring activity in the NO release assay.

TABLE 3

| Sample | Fresh Weight (g) | Total Volume (ml) | Protein Conc. (mg/ml) | Total Protein (mg) | Protein Yield (mg/gr) | Rprotein Conc. (Uml) | Total Rprotein (U) | Specific Yield (U/g) | Rprotein Yield (U/g) | % Recovery Rprotein In IF | X-Fold Purification |
|---|---|---|---|---|---|---|---|---|---|---|---|
| GCB/IF | 2.48 | 1.9 | 0.24 | 0.45 | 0.18 | 720 | 1368 | 552 | 3007 | 22 | 18 |
| GCB/H | 2.08 | 8.1 | 3.89 | 31.48 | 15.13 | 653 | 5289 | 2543 | 168 | ND | 1 |

IF = Interstitial fluid extraction
H = homogenization extraction
ND = Not determined

TABLE 4

| Greenhouse: | | | |
|---|---|---|---|
| Plant type | Av. Tissue Amt. | Interferon protein yield[1] | Yield activity[2] |
| *N. benthamiana* | 3–60 g | 1 mg/100 g fresh wt | ~30,000 U/ml IF |
| *N. tabacum* cv. MD609 | 20 g | 0.1 mg/100 g fresh wt | ~3,000 U/ml IF |
| Nitabacum TI231 | 20 g | 0.1 mg/100 g fresh wt | ~3,000 U/ml IF |

TABLE 5

| Field: | | | |
|---|---|---|---|
| Greenhouse Plant type | Av. Tissue Amt. | Interferon protein yield[1] | Yield activity[2] |
| *N. tabacum* cv TI264 | 80 g | 0.05 mg/100 g fresh wt | ND* |

TABLE 5-continued

Field:

| Greenhouse Plant type | Av. Tissue Amt. | Interferon protein yield[1] | Yield activity[2] |
|---|---|---|---|
| N. tabacum cv TI264 | 10 kg | 0.01 mg/100 g fresh wt | ~200 U/ml IF** |

[1]Interferon protein yield was estimated by quantitative immunoblotting.
[2]Interferon activity was determined by the NO release assay as described by Lowenthal et al. supra
*Not determined
**Activity estimates contained some lack of specificity (activity not neutralized by specific antibody) in NO release assay.

Example 5
Extraction of Mouse scFv Protein

Actively growing N. benthamiana were inoculated with infectious transcripts of a recombinant plant construct as described by Donson et al., supra, harboring a scFv protein from the 38C13 mouse lymphoma. Mouse 38C13 scFv protein was extracted from systemically infected leaves 11–14 days post inoculation.

Systemically infected leaves (3–80 grams) were detached from the plant at the leaf base, weighed, and placed in an appropriate sized beaker. The leaf material was completely covered with a buffered solution (100 mM Tris-HCl pH 7.5 buffer containing 10 mM $MgCl_2$ and 2 mM EDTA). The immersed leaves were covered with a Nalgene vacuum jar and a vacuum was pumped to 700 mm Hg, and held for 2 minutes and then rapidly released. This vacuum infiltration was then repeated for a total of two cycles. Following the vacuum infiltrations, the leaves were removed from the beaker and surface buffer was removed from the leaves' surface by blotting between absorbent paper. The interstitial fluid (IF) was recovered from the vacuum infiltrated leaves by centrifugation (3,000×G, 15 minutes). Leaves were centrifuged in a 250 ml bottle, containing a supported mesh which allows for the separation and recovery of the IF from the leaf material. The IF fluid containing the scFv protein was filtered through a 0.2 μm membrane and stored at −80° C.

The product and purification of 38C13 scFv protein from plant IF fluid was determined by Western analysis using S1C5, a monoclonal anti-idiotype antibody which recognizes native 38C13 IgM protein. The S1C5 antibody cross reacted with a 30 KD protein of the expected size of 38C13 scFv and a 60 KD protein, which is the correct size for a spontaneously assembling scFv dimer. No cross reactivity to plant proteins in IF extracts prepared from control infected plants was observed.

The quantity of plant-produced 38C 13 scFv protein recovered from IF extracts was measured by S1C5 ELISA. Leaf IF extracts were determined to contain 20–60 μg of 38C13 scFv protein/ml IF fluid or 11–30 μg of 38C13 scFv protein/g fresh weight. Since ELISA conditions favor anti-idiotype recognition in solution, it is concluded that the major fraction of 38C 13 scFv isolated from plant IF fluid is soluble and properly folded.

Example 6
Extraction of Secretory Immunoglobulin from Transgenic Tobacco

Leaves from transgenic, SIgA-G expressing N. tabacum (15 grams), (Science, 268:716, 1995), were detached from the plant at the leaf base, weighed, and placed in an appropriate sized beaker. The leaf material was completely covered with a buffered solution of either 100 mM Tris-Hcl pH 7.5 buffer containing 10 mM $MgCl_2$, 2 mM EDTA and 14.3 mM 2-mercaptoethanol or 100 mM potassium phosphate, pH6.0, 5 mM EDTA, 10.0 mM 2-mercaptoethanol and 0.5% taurocholic acid). The immersed leaves were covered with a Nalgene® vacuum jar and a vacuum was pumped to 750 mm Hg, and held for 1 minute and then rapidly released. Following the vacuum infiltrations, the leaves were removed from the beaker and surface buffer was removed from the leaves surface by blotting between absorbent paper. The interstitial fluid (IF) was recovered from the vacuum infiltrated leaves by centrifugation (1500×G, 15 minutes). Leaves were centrifuged in a 250 ml bottle, containing a supported mesh which allows for the separation and recovery of the IF from the leaf material.

Protein immunoblots of the IF extracts were prepared under reducing conditions. Ig was detected in the immunoblots using goat anti-mouse IgA conjugated to horseradish peroxidase. Approximately 10% of the IgA present in the plant was detected in the IF extracts. There was no visible difference in the quantity of Ig in the IF fractions produced using the different buffers described above. No cross reactivity to plant proteins in IF extracts prepared from control plants was observed.

Example 7
Pilot Scale Purification of Glucocerebrosidase from the Intercellular Fluid of Tobacco MD609 leaf tissue (1–2 kilograms) of transgenic tobacco expressing the lysosomal enzyme glucocerebrosidase was harvested, the mid vein removed and the tissue weighed. Tissue was submerged with 2–4 volumes of buffer (0.1 M $KPO_4$ buffer, pH 6.0, 5 mM EDTA, 0.5% taurocholic acid, 10 mM 2-mercaptoethanol) using an infiltration vessel that accommodates several kilograms of leaf tissue at one time. A perforated metal plate was placed on top of tissue to weigh down the tissue, and a vacuum was pumped to 620–695 mm Hg for 1–2 minutes×3. The vacuum was released between subsequent applications. Tissue was rotated and the vacuum reapplied to achieve complete infiltration. Multiple applications of the vacuum without isolating the interstitial fluid constitutes a single infiltration procedure. An indication of complete infiltration is a distinct darkening in color of the underside of the leaf tissue. Excess buffer on the tissue was drained. The interstitial fluid was released from the tissue by centrifuging the tissue in a basket rotor (10 in.×4.25 in., InterTest Equipment Services, San Jose, Calif./Biosource Design 25-0611000) at 4200 RPM (2500×G) for 10 minutes. The interstitial fluid was collected by aspiration (IF-1). Alternatively, the leaf tissue can be re-infiltrated by placing the leaves back in the infiltration vessel in the same buffer used above and the process repeated (IF-2). The second infiltration does not require as many cycles of vacuum infiltration and vacuum release. Additionally, the buffer may be drained from the infiltration vessel (spent buffer) and pooled with the 1st and 2nd IF fractions. Collectively, IF-1, IF-2 and spent buffer constitutes the IF pool. The volume of interstitial fluid collected from the infiltrated leaf tissue was between 50–100% of the leaf tissue by weight depending on the number of infiltrations carried out.

Recombinant GCB was purified by loading the dilute IF (feed stream) directly on a Pharmacia Streamline 25® column containing Phenyl Streamline® resin. Expanded bed chromatography enabled us to capture, clarify and concentrate our protein in one step without the need for centrifugation and/or microfiltration steps. The column was equilibrated and washed until the UV-signal on the recorder returned to baseline with 25 mM citrate, 20% ethylene glycol, pH 5.0; bound enzyme was eluted with 25 mM citrate, 70% ethylene glycol. The eluted material was further purified on a cation exchange resin, SP Big Beads® (Pharmacia), equilibrated in 25 mM citrate, 75 mM NaCl, pH 5.0. GCB was eluted with either a step gradient of 25 mM citrate, 0.5 M NaCl, 10% ethylene glycol, pH 5.0 or a linear gradient of 75 mM—0.4 M NaCl in 25 mM citrate, pH 5.0. All chromatography steps were carried out at room temperature.

Using the suicide substrate, conduritol β-epoxide (CBE), inhibition of recombinant glucocerebrosidase (rGCB) activity in the presence of plant glucosidases was achieved. Enzyme activity was measured at 37° C. in a reaction mixture containing 5 mM methylumbelliferyl β-D glucoside, 0.1 M Potassium Phosphate, 0.15% Triton-X100, 0.125% sodium taurocholate, 0.1% bovine serum albumin, pH 5.9 with and without CBE. Total glucosidase activity and rGCB activity were measured by hydrolysis of the fluorescent substrate 4-methylumbelliferyl glucopyranoside. One unit of activity is defined as the amount of enzyme required to catalyze the hydrolysis of 1 nmol of substrate per hour. Total protein was determined using the Bio-Rad Protein Assay based on the method of Bradford (Bradford, M. *Anal. Biochem.* 72:248; 1976).

Typically from 1 kilogram of leaves where IF-1 alone was collected we obtained 4 million units of GCB at a specific activity of 20,000. The Units/kg increased to 6 million with a lower specific activity of 10,000 when IF Pool was collected (IF-1, IF-2. and spent buffer).

Table 6 below contains data that is representative of several experiments.

Example 8

Ultrafiltration/Concentration of Intercellular Fluid from Tobacco Expressing Glucocerebrosidase 2.3 kilograms of MD609 leaf tissue from transgenic tobacco expressing the lysosomal enzyme glucocerebrosidase was harvested, the mid vein removed and the tissue weighed. Tissue was submerged with 24 volumes of buffer (0.1 M $KPO_4$ buffer, pH 6.0, 5 mM EDTA, 0.5% taurocholic acid, 10 mM 2-mercaptoethanol) in an infiltration vessel that accommodates several kilograms of leaf tissue at one time. A perforated metal plate was placed on top of tissue to weigh down the tissue. A vacuum was pumped to 620–695 mm Hg for 1–2 minutes×3. The vacuum was released between subsequent applications. Tissue was rotated and the vacuum reapplied to achieve complete infiltration. Excess buffer on the tissue was drained. The interstitial fluid was released from the tissue by centrifuging the tissue in a basket rotor (10 in.×4.25 in., Intertest Equipment Services, San Jose, Calif./Biosource Design 25-0611000) at 4200 RPM (2500× G) for 10 minutes. The interstitial fluid was collected by aspiration (IF-1). The leaf tissue was re-infiltrated by placing the leaves back in the infiltration vessel in the same buffer used above and the process repeated (IF-2). The buffer was drained from the infiltration vessel (spent buffer) and pooled with the 1st and 2nd IF fractions. Collectively, IF-1, IF-2 and spent buffer constitutes the IF pool. The IF pool was filtered through Miracloth and then concentrated 6 fold by passing the IF pool through a 1 sq. ft. spiral membrane (30K molecular weight cutoff) using an Amicon RA 2000® concentrator equipped with an LP-1 pump.

TABLE 6

GCB-Lab Pilot Scale IF Process

| Sample/Fraction # | Fresh Weight (Grams) | Total Vol (ml) | Protein Conc. (mg/ml) | Total Protein (mg) | GCB (mg) | Protein Yield (mg/g) | GCB Conc (U/ml) | Total GCB (Units) | Units/kg Tissue |
|---|---|---|---|---|---|---|---|---|---|
| IF1 | 1045 | 930 | 0.236 | 219 | 2.91 | 0.21 | 4,692 | 4,363,544 | 4,175,640 |
| Phenyl Streamline Apr. 30, 1997 | 1045 | 400 | 0.065 | 26 | 2.47 | 0.025 | 9,276 | 3,710,467 | 3,550,686 |
| IF1, 2 & Spent buffer | 1027 | 4020 | 0.29 | 1166 | 4.32 | 1.135 | 1,611 | 6,478,201 | 6,307,888 |
| IF1, 2 & SB Phenyl SL column load | 1027 | 2330 | 0.29 | 676 | 2.5 | 0.658 | 1,611 | 3,752,778 | 3,656,064 |
| Phenyl Streamline eluted material | 1027 | 400 | 0.078 | 31 | 2.36 | 0.03 | 8,858 | 3,543,390 | 3,450,234 |
| SP Big Beads eluant eluted material | 1027 | 70 | 0.078 | 5 | 1.72 | 0.005 | 36,952 | 2,586,674 | 2,518,670 |

| Sample/Fraction # | Sp Activity nmol/hr (U)/mg | % GCB % of total Protein = GCB | Step Recovery (%) | Step Purification fold | Total Recovery (%) | Total Purification fold |
|---|---|---|---|---|---|---|
| IF1 | 19,881 | 1.33 | 100 | 1 | 100 | 1 |
| Phenyl Streamline Apr. 30, 1997 | 142,710 | 9.51 | 85 | 7.2 | 85 | 7.2 |
| IF1, 2 & Spent buffer | 10,047 | 0.67 | 100 | 1 | 100 | 1 |
| IF1, 2 & SB Phenyl SL column load | 10,047 | 0.67 | 100 | 1 | 100 | 1 |
| Phenyl Streamline eluted material | 113,570 | 7.57 | 94.4 | 11.3 | 94.4 | 11.3 |
| SP Big Beads eluant eluted material | 473,750 | 31.58 | 73 | 4.2 | 68.9 | 47.2 |

IF = interstitial fluid

Using the suicide substrate, conduritol β-epoxide (CBE), inhibition of recombinant glucocerebrosidase (rGCB) activity in the presence of plant glucosidases was achieved. Enzyme activity was measured at 37° C. in a reaction mixture containing 5 mM methylumbelliferyl β-D glucoside, 0.1 M potassium phosphate, 0.15% Triton-X100, 0.125% sodium taurocholate, 0.1% bovine serum albumin, pH 5.9 with and without CBE. Total glucosidase activity and rGCB activity were measured by hydrolysis of the fluorescent substrate 4-methylumbelliferyl glucopyranoside. One unit of activity is defined as the amount of enzyme required to catalyze the hydrolysis of 1 nmol of substrate per hour. Total protein was determined using the Bio-Rad Protein Assay® based on the method of Bradford (Bradford, M. *Anal. Biochem.* 72:248; 1976). See Table 7 below.

Example 9
Pilot Scale Purification of Glucocerebrosidase from the Intercellular Fluid of Field Grown Tobacco 100 kilograms of MD609 leaf tissue from transgenic tobacco expressing the lysosomal enzyme glucocerebrosidase was harvested from the field each day for a period of two weeks. The tissue was stripped off the stalks by hand and weighed. Five kilograms of leaves were placed into polyester bags (Filtra-Spec®, 12-2-1053) and four×5 kg bags of leaves were placed into a metal basket. The metal basket containing the leaf material was placed in a 200 liter Mueller vacuum tank containing ~100 liters of buffered solution (0.1 $KPO_4$ buffer, pH 6.0, 5 mM EDTA, 0.5% taurocholic acid, 10 mM 2-mercaptoethanol). A 70 lb. stainless steel plate was placed over the leaves/bags to assure complete immersion. A vacuum was pumped to 695 mm Hg, held for 1 minute and then rapidly released. This vacuum infiltration was repeated for a total of two cycles. Multiple applications of the vacuum without isolating the interstitial fluid constitutes a single infiltration procedure. An indication of complete infiltration is a distinct darkening in color of the underside of the leaf tissue. Following the vacuum infiltrations, the leaves and basket were removed from the vacuum tank. The bags containing the vacuum infiltrated leaves were allowed to gravity drain surface buffer for ~10 minutes, prior to centrifugation. The interstitial fluid (IF) was recovered from the vacuum infiltrated leaves by centrifugation (1,800×G, 30 minutes) using a Heine® basket centrifuge (bowl dimensions, 28.0 inches diameter×16.5 inches).

Collected IF was filtered through a 50μ cartridge filter and then stored at 4° C., until the entire 100 kilograms of tissue was infiltrated. This process was repeated with the next set of four 5 kg bags (5×20 kg cycles total) until all the tissue was infiltrated. Additional buffer was added during each infiltration cycle to completely immerse the tissue. Alternatively, the leaf tissue can be re-infiltrated by placing the leaves back in the infiltration vessel in the same buffer used above and the process repeated (IF-2). Additionally, the buffer may be drained from the infiltration vessel (spent buffer) and may be pooled with the 1st and 2nd IF fractions. Collectively, IF-1, IF-2 and spent buffer constitutes the IF pool. The volume of interstitial fluid collected from the infiltrated leaf tissue was between 42–170% of the leaf tissue by weight depending on the number of infiltrations carried out.

Recombinant GCB was purified by loading the dilute interstitial fluid (feed stream) directly on a Pharmacia Streamline 200® column containing Phenyl Streamline® resin. Expanded bed chromatography enabled us to capture, clarify and concentrate our protein in one step without the need for centrifugation and/or microfiltration steps. The column was equilibrated and washed until the UV-signal on the recorder returned to baseline with 25 mM citrate, 20% ethylene glycol, pH 5.0; the bound enzyme was eluted with 25 mM citrate, 70% ethylene glycol. The eluted material was sterile filtered by passing the eluted material through a 1 sq. ft. 0.8 um Sartoclean GF® capsule followed by a 1 sq. ft. 0.2 um Sartobran P® sterile filter (Sartorius, Corp.) and stored at 4° C. until the next chromatography step. The eluted material from 4–5 days of Phenyl Streamline® chromatography runs was pooled together and further purified on a cation exchange resin, SP Big Beads® (Pharmacia), equilibrated in 25 mM citrate, 75 mM NaCl, pH 5.0. GCB was eluted with a step gradient of 25 mM citrate, 0.4 M NaCl, 10% ethylene glycol, pH 5.0. All chromatography steps were carried out at room temperature. The eluted material was sterile filtered by passing the eluted material through a 1 sq. ft. 0.8 urn Sartoclean GF® capsule followed by a 1 sq. ft. 0.2 um Sartobran P® sterile filter (Sartorius, Corp.) and stored at 4° C.

Using the suicide substrate, conduritol β-epoxide (CBE), inhibition of recombinant glucocerebrosidase (rGCB) activity in the presence of plant glucosidases was achieved. Enzyme activity was measured at 37° C. in a reaction mixture containing 5 mM methylumbelliferyl β-D glucoside, 0.1 M Potassium Phosphate, 0.15% Triton-X100, 0.125% sodium taurocholate, 0.1% bovine serum albumin, pH 5.9 with and without CBE. Total glucosidase activity and rGCB activity were measured by hydrolysis of the fluorescent substrate 4-methylumbelliferyl glucopyranoside. Total protein was determined using the Bio-Rad Protein Assay®

TABLE 7

| | GCB UF Experiment | | | | | | | | |
|---|---|---|---|---|---|---|---|---|---|
| Sample/Fraction # | Fresh Weight (Grams) | Total Vol (ml) | Protein Conc. (mg/ml) | Total Protein (mg) | GCB (mg) | Protein Yield (mg/g) | GCB Conc (U/ml) | Total GCB (Units) | Units/kg Tissue |
| IF | 1,102 | 5,874 | 0.223 | 1310 | 6.5 | 1.189 | 1,659 | 9,745,470 | 8,843,439 |
| 30 K Concentrate | 1,102 | 875 | 0.593 | 519 | 6.39 | 0.471 | 10,947 | 9,578,575 | 8,691,992 |

| Sample/Fraction # | Sp Activity nmol/hr ((U)/mg) | % GCB % of total Protein = GCB | Step Recovery (%) | Step Purification fold | Total Recovery (%) | Total Purification fold |
|---|---|---|---|---|---|---|
| IF | 7,440 | 0.5 | 100 | 1 | 100 | 1 |
| 30 K Concentrate | 18,460 | 1.23 | 98.3 | 2.5 | 98.3 | 2.5 |

IF = interstitial fluid based on the method of Bradford (Bradford, M. *Anal. Biochem.* 72:248; 1976).

Typically from 1 kilogram of field grown tobacco, expressing GCB, where IF-1 alone was collected we obtained 435,000 units of GCB at a specific activity of 2,745 units. The Unit/kg increased to 755,000 with a specific activity of 3,400 when IF Pool was collected (IF-1, IF-2 and spent buffer).

Table 8 below contains data that is representative of one week of experiments.

leaf material was placed in a 200 liter Mueller® vacuum tank containing ~100 liters of buffered solution (0.1 $KPO_4$ buffer, pH 6.0, 5 mM EDTA, 0.5% taurocholic acid, 10 mM 2-mercaptoethanol). A 70 lb. stainless steel plate was placed over the leaves/bags to assure complete immersion. A vacuum was pulled 695 mm Hg, held for 1 minute and then rapidly released. This vacuum infiltration was repeated for a total of two cycles. Following the vacuum infiltrations, the leaves and basket were removed from the vacuum tank. The bags containing the vacuum infiltrated

TABLE 8

GCB Field Test Pilot Scale-P.SL

| Sample/Fraction # | Fresh Weight (Grams) | Total Vol (ml) | Protein Conc. (mg/ml) | Total Protein (Mg) | GCB (mg) | Protein Yield (mg/g) | GCB Conc U/ml | Total GCB (Units) |
|---|---|---|---|---|---|---|---|---|
| IF1, 2 & SB - Day 1 | 100,000.00 | 164,500 | 0.12 | 19740 | 49.24 | 0.197 | 449 | 73,860,500 |
| Phenyl Streamline eluded material | 100,000.00 | 37,600 | 0.04 | 1504 | 5.84 | 0.015 | 233 | 8,760,800 |
| IF1, 2 & SB - Day 2 | 100,000.00 | 171,000 | 0.144 | 24624 | 51.41 | 0.246 | 451 | 77,121,000 |
| Phenyl Streamline eluted material | 100,000.00 | 42,500 | 0.036 | 1530 | 8.67 | 0.015 | 306 | 13,005,000 |
| IF1, 2 - Day 3 | 100,000.00 | 95,500 | 0.547 | 52239 | 39.16 | 0.522 | 615 | 58,732,500 |
| Phenyl Streamline eluted material | 100,000.00 | 34,000 | 0.059 | 2006 | 22.05 | 0.02 | 973 | 33,082,000 |
| IF1 - Day 4 | 100,000.00 | 50,000 | 0.273 | 13650 | 20.23 | 0.137 | 607 | 30,350,000 |
| Phenyl Streamline eluted material | 100,000.00 | 35,800 | 0.046 | 1647 | 14.77 | 0.016 | 619 | 22,160,200 |
| IF1 - Day 5 | 100,000.00 | 86,000 | 0.348 | 29928 | 35.03 | 0.299 | 611 | 52,546,000 |
| Phenyl Streamline eluted material | 100,000.00 | 40,700 | 0.065 | 2646 | 19.73 | 0.226 | 727 | 29,588,900 |
| SP Big Beads - 5 days of PSL runs | 500,000.00 | 191,650 | 0.053 | 10157 | 62.08 | 0.02 | 486 | 93,113,911 |
| SP Big Beads eluted material | 500,000.00 | 17,000 | 0.043 | 731 | 48.35 | 0.001 | 4,266 | 72,529,928 |

| Sample/Fraction # | Units/kg Tissue | Sp Activity nmol/hr ((U)/mg) | % GCB % of total Protein = GCB | Step Recovery (%) | Step Purification fold | Total Recovery (%) | Total Purification fold |
|---|---|---|---|---|---|---|---|
| IF1, 2 & SB - Day 1 | 738,605 | 3,742 | 0.25 | 100 | 1 | 100 | 1 |
| Phenyl Streamline eluded material | 87,608 | 5,825 | 0.39 | 11.9 | 1.6 | 11.9 | 1.6 |
| IF1, 2 & SB - Day 2 | 77,121,000 | 3,132 | 0.21 | 100 | 1 | 100 | 1 |
| Phenyl Streamline eluted material | 13,005,000 | 8,500 | 0.57 | 16.9 | 2.7 | 16.9 | 2.7 |
| IF1, 2 - Day 3 | 58,732,500 | 1,124 | 0.07 | 100 | 1 | 100 | 1 |
| Phenyl Streamline eluted material | 33,082,000 | 16,492 | 1.1 | 56.3 | 14.7 | 56.3 | 14.7 |
| IF1 - Day 4 | 30,350,000 | 2,223 | 0.15 | 100 | 1 | 100 | 1 |
| Phenyl Streamline eluted material | 22,160,200 | 13,457 | 0.9 | 73 | 6.1 | 73 | 6.1 |
| IF1 - Day 5 | 52,546,000 | 1,756 | 0.12 | 100 | 1 | 100 | 1 |
| Phenyl Streamline eluted material | 29,588,900 | 11,185 | 0.75 | 56.3 | 6.4 | 56.3 | 6.4 |
| SP Big Beads - 5 days of PSL runs | 93,113,911 | 9,167 | 0.61 | 100 | 1 | 100 | 1 |
| SP Big Beads eluted material | 72,529,928 | 99,220 | 6.61 | 77.9 | 10.8 | 77.9 | 10.8 |

Example 10

Chopped Tissue Experiment

An experiment was carried out where 100 kilograms of MD609 leaf tissue of transgenic tobacco expressing the lysosomal enzyme glucocerebrosidase was harvested off the stalks by hand, weighed and chopped into small pieces to increase the surface area for buffer infiltration. Five kilograms of leaves were placed into polyester bags (Filtra-Spec®, 12-2-1053) and four×5 kg bags of leaves were placed into a metal basket. The metal basket containing the leaves were allowed to gravity drain surface buffer for ~10 minutes, prior to centrifugation. The interstitial fluid (IF) was recovered from the vacuum infiltrated leaves by centrifugation (1,800×G, 30 minutes) using a Heine® basket centrifuge (bowl dimensions, 28.0 inches diameter×16.5 inches). Collected IF was filtered through a 50μ cartridge filter and then stored at 4° C., until the entire 100 kilograms of tissue was infiltrated. This process was repeated with the next set of four 5 kg bags (5 cycles×20 kg cycles total) until all the tissue was infiltrated. Additional buffer was added during each infiltration cycle to completely immerse the tissue. In order to evaluate how much enzyme was recovered in the interstitial fluid, the tissue from which the interstitial fluid was isolated was then homogenized in a Waring® blender with 4 volumes of the same infiltration buffer as above, centrifuged and the supernatant assayed for enzyme activity.

Recombinant GCB was purified by loading the dilute interstitial fluid (feed stream) directly on a Pharmacia Streamline 200® column containing Phenyl Streamline® resin. The column was equilibrated and washed until UV-signal on recorder returned to baseline with 25 mM citrate, 20% ethylene glycol, pH 5.0 and then eluted with 25 mM citrate, 70% ethylene glycol. All chromatography steps were carried out at room temperature Table 9 below contains data from the chops experiment.

Example 11
Pilot Scale Purification of Alpha Galactosidase from the Intercellular Fluid of Nicotiana benthamiana Actively growing Nicotiana benthamiana plants were inoculated with infectious transcripts of a recombinant plant viral construct containing the lysosomal enzyme alpha galactosidase gene wherein the α-galuctosidase gene contains a carboxy-terminal modification to the nucleotide sequence to enable secretion to the interstitial space. Systemically infected leaf tissue (1–2 kilograms) was harvested from Nicotiana benthamiana expressing alpha galactosidase 14 days post inoculation. The tissue was weighed and submerged with 2–4

Alternatively, petioles and stems have been harvested along with the leaf tissue for infiltration. The mid vein was not removed from the tissue prior to infiltration.

Alpha galactosidase was purified by loading the dilute intercellular (feed stream) directly onto a Pharmacia Streamline 25® column containing Butyl Streamline® resin. Expanded bed chromatography enabled the capture, clarification and concentration of the protein in one step without the need for centrifugation and/or microfiltration steps. The column was equilibrated and washed until UV-signal on recorder returned to baseline with 25 mM bis tris propane, pH 6.0 20% $(NH_4)_2SO_4$ and then eluted with 25 mM bis tris propane, pH 6.0. The eluted material was further purified on hydroxyapatite equilibrated with 1 mM $NaPO_4$ buffer, 5% glycerol, pH 6.0 and eluted with either a 1–250 mM $NaPO_4$ buffer, 5% glycerol, pH 6.0 linear gradient or a step gradient. All chromatography steps were carried out at room temperature.

Alpha galactosidase activity was measured by hydrolysis of the fluorescent substrate 4-methylumbelliferyl α-D galactopyranoside. Enzyme activity was measured at 37° C. in a reaction mixture containing 5 mM methylumbelliferyl α-D galactopyranoside, 0.1 M potassium phosphate, 0.15% Triton-X100®, 0.125% sodium taurocholate, 0.1% bovine serum albumin, pH 5.9. Total protein was determined using the Bio-Rad Protein Assay® based on the method of Bradford (Bradford, M. *Anal. Biochem.* 72:248; 1976).

From 1 kilogram of leaves, we typically obtain between 140–160 million units of alpha galactosidase at a specific

TABLE 9

GCB Field Test Chops

| Sample/Fraction # | Fresh Weight (Grams) | Total Vol (ml) | Protein Conc. (mg/ml) | Total Protein (mg) | GCB (mg) | Protein Yield (mg/g) | GCB Conc (U/ml) | Total GCB (Units) |
|---|---|---|---|---|---|---|---|---|
| IF1/Chops | 100,000.00 | 56,000 | 0.678 | 37946 | 10.42 | 0.379 | 279 | 15,624,000 |
| Phenyl Streamline eluded material | 100,000.00 | 30,000 | 0.072 | 2147 | 9.38 | 0.021 | 469 | 14,070,000 |
| Tissue Homogenate | 100,000.00 | 56,000 | ND | ND | 15.08 | 0 | 404 | 22,621,081 |

| Sample/Fraction # | Units/kg Tissue | Sp Activity nmol/hr ((U)/mg) | % GCB % of total Protein = GCB | Step Recovery (%) | Step Purification fold | Total Recovery (%) | Total Purification fold |
|---|---|---|---|---|---|---|---|
| IF1/Chops | 156,240 | 412 | 0.03 | 100 | 1 | 100 | 1 |
| Phenyl Streamline eluded material | 140,700 | 6,553 | 0.44 | 90.1 | 15.9 | 90.1 | 15.9 |
| Tissue Homogenate | 226,211 | ND | ND | ND | ND | ND | ND |

ND = not determined volumes of buffer (25 mM bis tris propane buffer, pH 6.0, 5 mM EDTA, 0.1 M NaCl, 10 mM 2-mercaptoethanol) in an infiltration vessel that can accommodate several kilograms of leaf tissue at one time. A perforated metal plate was placed on top of tissue to weigh down the tissue. A vacuum was pumped to 620–695 mm Hg for 30 seconds and then quickly released. The tissue was rotated and the vacuum reapplied to achieve complete infiltration which was confirmed by a distinct darkening in color of the underside of the leaf tissue. Excess buffer on the tissue was drained. The interstitial fluid was released from the tissue by centrifuging the tissue in a basket rotor (10 in.×4.25 in. Depth, InterTest Equipment Services, San Jose, Calif./Biosource Design 25-0611000) at 3800 RPM (2100×G) for 10–15 minutes. The interstitial fluid was collected by aspiration. In some instances only infected leaf tissue was harvested.

activity of 800,000 units following a single infiltration procedure (IF-1).

Table 10 below contains data that is representative of several experiments.

Example 12
Pilot Scale Purification of Glucocerebrosidase from the Leaf Interstitial Fluid and of Recombinant Virus from the Leaf Homogenate of Field Grown Tobacco Transgenic tobacco (MD609) expressing the lysosomal enzyme glucocerebrosidase was mechanically inoculated with a tobacco mosaic virus derivative containing a coat protein loop fusion, TMV291, (Turpen, et.al., 1995, *Bio/Technology* 13:23–57). A total of 100 kg of transgenic, transfected leaf tissue was harvested from the field, five weeks post inoculation. The tissue was stripped off the stalks by hand and weighed. Five kilograms of leaves were placed into polyester bags (Filtra-Spec®, 12-2-1053) and four×5 kg bags of leaves were placed into a metal basket. The metal basket containing the leaf material was placed in a 200 liter Mueller® vacuum tank containing ~100 liters of buffered solution (0.1 KPO$_4$ buffer, pH 6.0, 5 mM EDTA, 0.5% taurocholic acid, 10 mM 2-mercaptoethanol). A 70 lb. stainless steel plate was placed over the leaves/bags to assure complete immersion. A vacuum was pumped to 695 mm Hg, held for 1 minute and then rapidly released. This vacuum infiltration was repeated for a total of two cycles. Multiple applications of the vacuum without isolating the interstitial fluid constitutes a single infiltration procedure. An indication of complete infiltration is a distinct darkening in color of the underside of the leaf tissue. Following the vacuum infiltrations, the leaves and basket were removed from the vacuum tank. The bags containing the vacuum infiltrated leaves were allowed to gravity drain surface buffer for ~10 minutes, prior to centrifugation. The interstitial fluid (IF) was recovered from the vacuum infiltrated leaves by centrifugation (1,800×G, 30 minutes) using a Heine® basket centrifuge (bowl dimensions, 28.0 inches diameter×16.5 inches). Collected IF was filtered through a 50μ cartridge filter and then stored at 4° C., until the entire 100 kilograms of tissue was infiltrated. This process was repeated with the next set of four 5 kg bags (5 cycles×20 kg total) until all the tissue was infiltrated. Additional buffer was added during each infiltration cycle to completely immerse the tissue.

Recombinant GCB was purified by loading the dilute intercellular (feed stream) directly on a Pharmacia Streamline 200® column containing Phenyl Streamline® resin. Expanded bed chromatography enabled the capture, clarification and concentration the protein in one step without the need for centrifugation and/or microfiltration steps. The column was equilibrated and washed until the UV-signal on the recorder returned to baseline with 25 mM citrate, 20% ethylene glycol, pH 5.0; the bound enzyme was eluted with 25 mM citrate, 70% ethylene glycol. The eluted material was sterile filtered by passing the eluted material through a 1 sq. ft. 0.8 μm Sartoclean GF® capsule followed by a 1 sq. ft. 0.2 μm Sartobran P® sterile filter (Sartorius, Corp.) and stored at 4° C. until the next chromatography step. The eluted material from 4–5 days of Phenyl Streamline® chromatography runs was pooled together and further purified on a cation exchange resin, SP Big Beads® (Pharmacia), equilibrated in 25 mM citrate, 75 mM NaCl, pH 5.0. GCB was eluted with a step gradient of 25 mM citrate, 0.4 M NaCl, 10% ethylene glycol, pH 5.0. All chromatography steps were carried out at room temperature. The eluted material was sterile filtered by passing the eluted material through a 1 sq. ft. 0.8 um Sartoclean GF® capsule followed by a 1 sq. ft. 0.2 μm Sartobran P® sterile filter (Sartorius, Corp.) and stored at 4° C.

Using the suicide substrate, conduritol β-epoxide (CBE), inhibition of recombinant glucocerebrosidase (rGCB) activity in the presence of plant glucosidases was achieved. Enzyme activity was measured at 37° C. in a reaction mixture containing 5 mM methylumbelliferyl β-D glucoside, 0.1 M potassium phosphate, 0.15% Triton-X 100®, 0.125% sodium taurocholate, 0.1% bovine serum albumin, pH 5.9 with and without CBE. Total glucosidase activity and rGCB activity were measured by hydrolysis of the fluorescent substrate 4-methylumbelliferyl glucopyranoside. Total protein was determined using the Bio-Rad Protein Assay® based on the method of Bradford (Bradford, M. *Anal. Biochem.* 72:248 (1976)).

TABLE 10

Pilot Scale alpha gal

| Sample/Fraction # | Fresh Weight (Grams) | Total Vol (ml) | Protein Conc. (mg/ml) | Total Protein (mg) | Gal (mg) | Protein Yield (mg/g) | Gal Conc (U/ml) | Total Gal (Units) |
|---|---|---|---|---|---|---|---|---|
| IF | 2026 | 1,450 | 0.236 | 342 | 74.5 | 0.169 | 226,201 | 327,992,085 |
| Butyl Streamline eluted material | 2026 | 300 | 0.392 | 118 | 74 | 0.058 | 1,085,873 | 325,761,839 |
| Hydroxyapatite eluted material | 2026 | 470 | 0.076 | 36 | 54.2 | 0.018 | 507,640 | 238,590,619 |

| Sample/Fraction # | Units/kg tissue | Sp Activity Nmol/hr ((U)/mg) | % Gal % of total Protein = Gal | Step Recovery (%) | Step Purification fold | Total Recovery (%) | Total Purification fold |
|---|---|---|---|---|---|---|---|
| IF | 161,891,454 | 958,481 | 21.78 | 100 | 1 | 100 | 1 |
| Butyl Streamline eluted material | 160,790,641 | 2,770,084 | 62.96 | 99.3 | 2.9 | 99.3 | 2.9 |
| Hydroxyapatite eluted material | 117,764,373 | 6,679,469 | 151.81 | 73.2 | 2.4 | 72.7 | 7 |

IF = interstitial fluid extraction

The quantity remaining of virus present in IF extracted leaf tissue was determined using homogenization and polyethylene glycol precipitation methods. In addition, the amount of virus present in the pooled, interstitial fluid was determined by direct polyethylene glycol precipitation. Final virus yields from precipitated samples was determined spectrophotometrically by absorbance at 260 nm. (see Table 11)

TABLE 11

| Sample | Virus Titer |
|---|---|
| Pooled IF | 0.004 mg virus/g fresh weight, 0.010 mg virus/ml IF |
| Homogenized leaf tissue following IF Extraction | 0.206 mg virus/g fresh weight |

Table 12 contains the GCB recovery data from TMV transfected plant tissue.

This example demonstrates the ability to extract two different products from the same leaf tissue based upon extraction procedures that specifically target products localized in the apoplast and cytosol.

While the invention of this patent application is disclosed by reference to the details of preferred embodiments of the invention, it is to be understood that this disclosure is intended in an illustrative, rather than limiting, sense. It is contemplated that modifications will readily occur to those skilled in the art, within the spirit of the invention and the scope of the appended claims. It is further understood that the instant invention applies to all proteins produced or capable of being recombinantly produced in plants, and is clearly not limited to those proteins specifically described herein.

Example 13
Large Scale Centrifugation of IF Fractions

The following example illustrates a scale-up procedure for the production of IF extract

TABLE 12

GCB Recovery From TMV Transfected Plants

| Sample/Fraction # | Fresh Weight (Grams) | Total Vol (ml) | Protein Conc. (mg/ml) | Total Protein (mg) | GCB (mg) | Protein Yield (Mg/g) | GCB Conc (U/ml) | Total GCB (Units) |
|---|---|---|---|---|---|---|---|---|
| IF1/Virus | 100,000 | 40,000 | 0.383 | 15320 | 18.7 | 0.153 | 701 | 28,055,851 |
| Phenyl Streamline eluted material | 100,000 | 25,000 | 0.024 | 600 | 6.66 | 0.006 | 400 | 9,990,926 |

| Sample/Faction # | Units/kg tissue | Sp Activity nmol/hr ((U)/mg) | % GCB % of total Protein | Step Recovery (%) | Step Purification fold | Total Recovery (%) | Total Purification Fold |
|---|---|---|---|---|---|---|---|
| IF1/Virus | 280,559 | 1,831 | 0.12 | 100 | 1 | 100 | 1 |
| Phenyl Streamline eluted material | 99,909 | 16,652 | 1.11 | 35.6 | 9.1 | 35.6 | 9.1 | using a discontinuous batch method that will produce a constant stream of IF extract to downstream processing. This procedure consists of the following elements:
1. Automated Whole Leaf Harvesting
2. Large Scale Continuous Infiltration
3. Large Scale Basket Centrifugation There are at least two full-scale, whole leaf harvester designs available. One has been developed by R. J. Reynolds Company and has been used at their Avoca facility in North Carolina. The other harvester has been developed by University of Kentucky, Agricultural Engineering department and has been demonstrated for three seasons in Daviess County Kentucky in commercial tobacco fields. These harvesters have shown the capablilty to cut intact plants, strip-off whole leaves and separate the leaves and stem tissue at rates over several acres per hour. The leaves will then be transported to the extraction facility in trailers.

Figure 2:
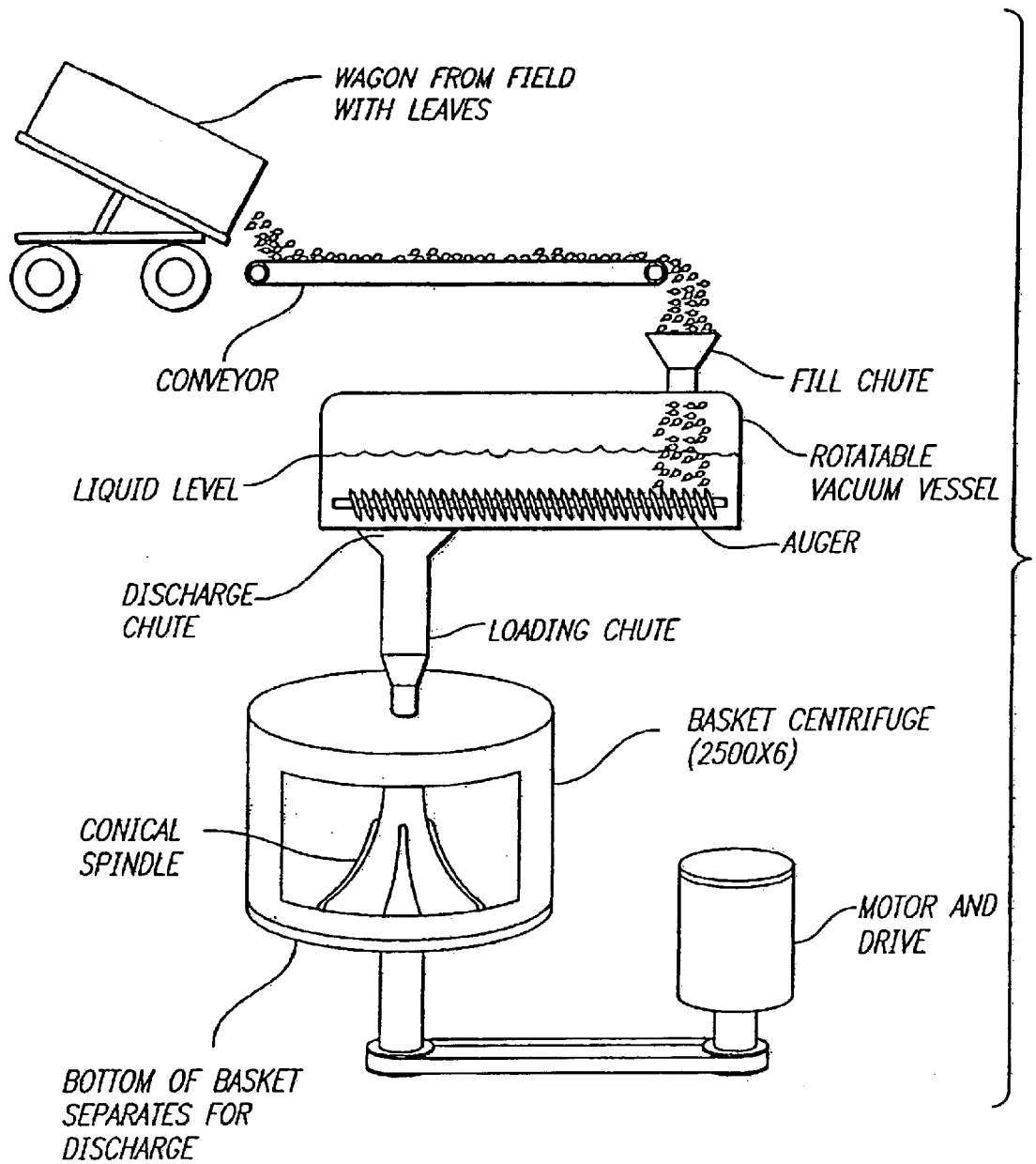
FIG. 2 Batch Vessel Infiltration
Figure 3:
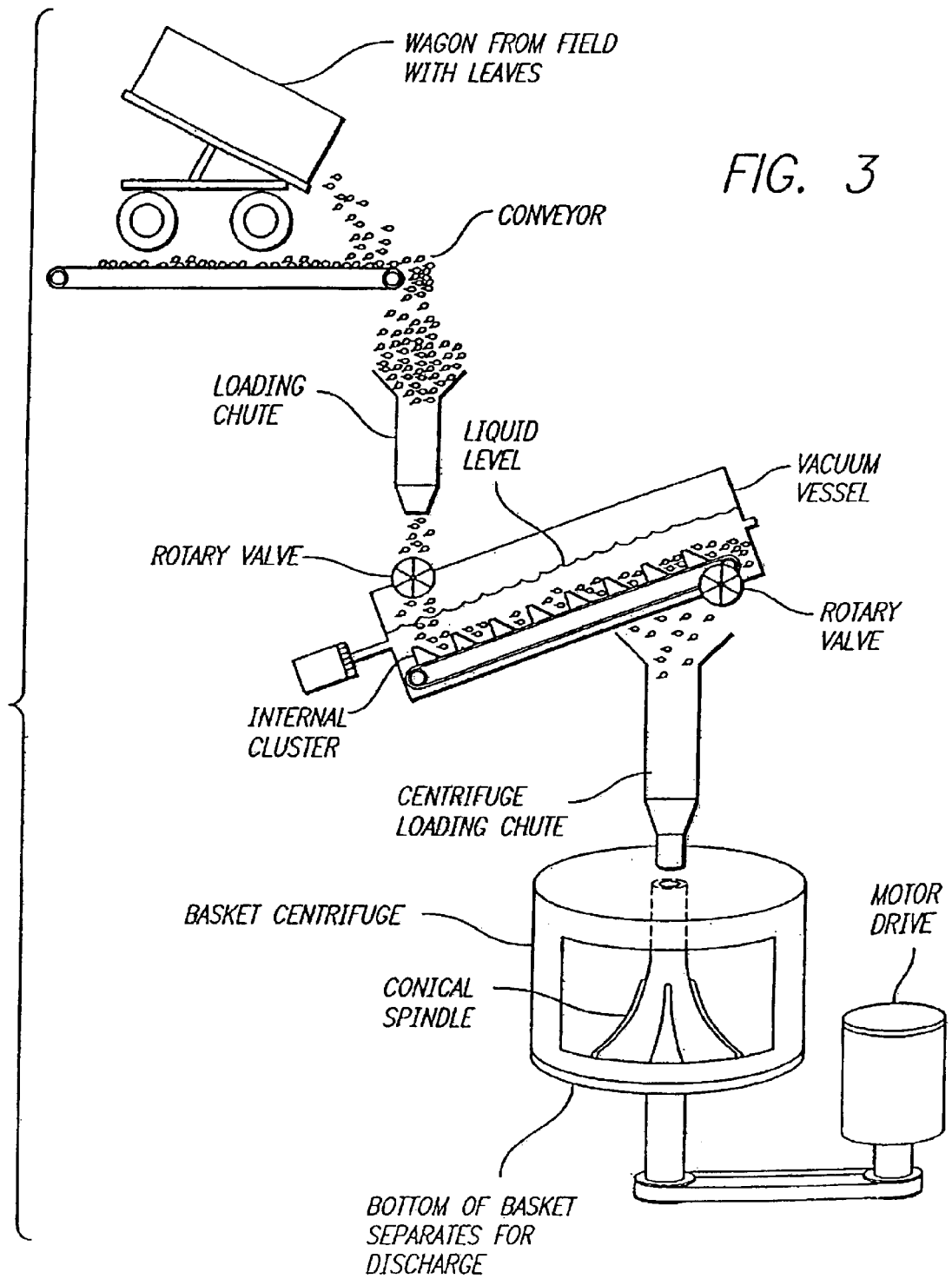
FIG. 3 Continuous Vacuum Infiltration

The leaves will then be unloaded by mechanical conveyor and continuous weigh belt feeder into the vacuum infiltration system. Two systems have been designed. System 1 (FIG. 1) is a bulk tank. This tank is constructed for full vacuum and is rotatable at low (less than 50) rpm so that all leaves are immersed in the infiltration medium. A vacuum is created by conventional mechanical vacuum pumps or by a steam ejector to a vacuum equal to 21 inches of water column pressure. The vacuum is then released causing infiltration of the tissue. The vessel is then drained to a secondary tank for buffer reuse and the leaf tissue is discharged from the vessel via an auger in the bottom of the tank to a discharge port and onto a conveyor. This conveyor transports the leaves to the basket centrifuge via a weigh belt. The weigh belt insures that a measured amount of material is added to the centrifuge for each centrifugations cycle. System 2 is a continuous vacuum infiltration system. This system consists of large cylindrical tube that has an internal auger conveyor (FIG. 2). The cylinder is placed at an angle. The cylinder is partially filled with the infiltration fluid. The cylinder is under vacuum provided by conventional vacuum pumps or a steam ejector to approximately 21 inches of water column pressure. Leaf tissue is added through a rotary valve that maintains the vacuum as it adds tissue. The leaf tissue is then immersed for a period of time in the buffer as it travels up the tube, conveyed by the auger. The infiltrated leaves are discharged at the elevated end of the auger through another rotary valve. At this point the vacuum is released. This type of pressure vessel, equipped with rotary valves and an auger transport flight is adapted from a pressure vessel design by Christian Engineering (San Francisco) that is used for continuous cooking of rice and other materials using steam pressure. Once discharged, the leaves are transported to the basket centrifuge via a conveyor equipped with a weigh belt. The weigh belt functions as stated above to insure the proper charge of material for each cycle of the basket centrifuge.

The basket centrifuge is a modification of a basic Sanborn (UPE) design for the vegetable industry for dewatering salad greens after washing. The centrifuge is a basket design with a cone type spindle on the inside of the basket. The basket is a two piece design that accomplishes the separation of the bottom plate from the cylinder via a hydraulic piston. The centrifuge is loaded at very low speed (i.e., low RPM or low G force) via a conveyor that is placed over the center of the basket equipped with the cone spindle. As the material drops from the conveyor it is deflected by the cone evenly upon the side of the perforated basket. When the charge of the leaves is complete the auger stops and the basket is accelerated to 2000–2500 ×G for approximately 5–60 min. The IF fluid is recovered from the centrifuge. At the end of the centrifugation the basket is decelerated to a low rpm. The bottom of the basket is separated from the sides (cylinder) by the action of the hydraulic piston. The leaf tissue is discharged to a conveyor, the bottom of the centrifuge is closed and the cycle is repeated. This design requires that a rotor and drive be designed that can be rated for the higher G force. Typically the Sanbom type machines are only rated for 600 to 800 G. It is, however, within normal engineering parameters to construct such an upgraded machine for this unique application.

What is claimed is:

1. A method for recovery of a concentrated protein or bio-molecule of interest from the interstitial fluid of a plant tissue comprising the steps of:
   (a) submerging plant tissue in buffer solution;
   (b) subjecting the plant tissue and buffer solution to a substantially vacuum environment and rapidly releasing the vacuum;
   (c) separating the plant tissue from the buffer solution;
   (d) centrifuging the tissue to remove interstitial fluid; and
   (e) concentrating the protein or bio-molecule of interest from the interstitial fluid;
   wherein said plant tissue are either one of the following: harvested whole plant leaves, and plant leaves dissected substantially along the midrib thereof.

2. A method of claim 1, wherein said whole plant leaves are harvested from any one of the following plants: *Nicotiana benthamiana* and *Nicotiana tabacum*.

3. A method of claim 1, wherein said step of subjecting the plant tissue and buffer solution to a substantially vacuum environment is repeated at least once before said separating step.

4. The method of claim 1, wherein the protein of interest is produced in the plant by a recombinant plant viral vector.

5. The method of claim 1, wherein the host plant is a transgenic plant that produces the protein or bio-molecule.

6. The method of claim 1, wherein the protein of interest is produced through transfection of the host plant.

7. The method of claim 1, wherein the protein of interest is selected from any one of the following: a human lysosomal enzyme; an industrial enzyme; a cytokine; an antibody or antibody fragment; α-galactosidase or an isozyme of α-galactosidase; glucocerebrosidase or an isozyme of glucocerebrosidase; a signaling peptide to direct the protein to a specific compartment within a cell.

8. A method of claim 1, further comprising the step of harvesting plant tissue before said submerging step.

* * * * *

SEQUENCE LISTING

<160> NUMBER OF SEQ ID NOS: 1

<210> SEQ ID NO 1
<211> LENGTH: 7926
<212> TYPE: DNA
<213> ORGANISM: VIRAL

<400> SEQUENCE: 1

| | | | | | | |
|---|---|---|---|---|---|---|
| gtattttac | aacaattacc | aacaacaaca | acaacaaac | aacattacaa | ttactatta | 60 |
| caattacaat | ggcatacaca | cagacagcta | ccacatcagc | tttgctggac | actgtccgag | 120 |
| gaaacaactc | cttggtcaat | gatctagcaa | agcgtcgtct | ttacgacaca | gcggttgaag | 180 |
| agtttaacgc | tcgtgaccgc | aggcccaagg | tgaacttttc | aaaagtaata | agcgaggagc | 240 |
| agacgcttat | tgctacccgg | gcgtatccag | aattccaaat | tacattttat | aacacgcaaa | 300 |
| atgccgtgca | ttcgcttgca | ggtggattgc | gatctttaga | actggaatat | ctgatgatgc | 360 |
| aaattcccta | cggatcattg | acttatgaca | taggcgggaa | ttttgcatcg | catctgttca | 420 |
| agggacgagc | atatgtacac | tgctgcatgc | ccaacctgga | cgttcgagac | atcatgcggc | 480 |
| acgaaggcca | gaaagacagt | attgaactat | acctttctag | gctagagaga | ggggggaaaa | 540 |
| cagtccccaa | cttccaaaag | gaagcatttg | acagatacgc | agaaattcct | gaagacgctg | 600 |
| tctgtcacaa | tactttccag | acaatgcgac | atcagccgat | gcagcaatca | ggcagagtgt | 660 |
| atgccattgc | gctacacagc | atatatgaca | taccagccga | tgagttcggg | gcggcactct | 720 |
| tgaggaaaaa | tgtccatacg | tgctatgccg | ctttccactt | ctctgagaac | ctgcttcttg | 780 |
| aagattcata | cgtcaatttg | gacgaaatca | acgcgtgttt | ttcgcgcgat | ggagacaagt | 840 |
| tgacctttc | ttttgcatca | gagagtactc | ttaattattg | tcatagttat | tctaatattc | 900 |
| ttaagtatgt | gtgcaaaact | tacttcccgg | cctctaatag | agaggtttac | atgaaggagt | 960 |
| ttttagtcac | cagagttaat | acctggtttt | gtaagttttc | tagaatagat | acttttcttt | 1020 |
| tgtacaaagg | tgtggcccat | aaaagtgtag | atagtgagca | gttttatact | gcaatggaag | 1080 |
| acgcatggca | ttacaaaaag | actcttgcaa | tgtgcaacag | cgagagaatc | ctccttgagg | 1140 |
| attcatcatc | agtcaattac | tggttttccca | aaatgaggga | tatggtcatc | gtaccattat | 1200 |
| tcgacatttc | tttggagact | agtaagagga | cgcgcaagga | agtcttagtg | tccaaggatt | 1260 |
| tcgtgtttac | agtgcttaac | cacattcgaa | cataccaggc | gaaagctctt | acatacgcaa | 1320 |
| atgttttgtc | ctttgtcgaa | tcgattcgat | cgagggtaat | cattaacggt | gtgacagcga | 1380 |
| ggtccgaatg | ggatgtggac | aaatctttgt | tacaatcctt | gtccatgacg | ttttacctgc | 1440 |
| atactaagct | tgccgttcta | aaggatgact | tactgattag | caagtttagt | ctcggttcga | 1500 |
| aaacggtgtg | ccagcatgtg | tgggatgaga | tttcgctggc | gtttgggaac | gcatttccct | 1560 |
| ccgtgaaaga | gaggctcttg | aacaggaaac | ttatcagagt | ggcaggcgac | gcattagaga | 1620 |
| tcagggtgcc | tgatctatat | gtgaccttcc | acgacagatt | agtgactgag | tacaaggcct | 1680 |
| ctgtggacat | gcctgcgctt | gacattagga | gaaagatgga | agaaacggaa | gtgatgtaca | 1740 |
| atgcactttc | agagttatcg | gtgttaaggg | agtctgacaa | attcgatgtt | gatgtttttt | 1800 |
| cccagatgtg | ccaatctttg | gaagttgacc | caatgacggc | agcgaaggtt | atagtcgcgg | 1860 |
| tcatgagcaa | tgagagcggt | ctgactctca | catttgaacg | acctactgag | gcgaatgttg | 1920 |
| cgctagcttt | acaggatcaa | gagaaggctt | cagaaggtgc | tttggtagtt | acctcaagag | 1980 |
| aagttgaaga | accgtccatg | aagggttcga | tggccagagg | agagttacaa | ttagctggtc | 2040 |

-continued

```
ttgctggaga tcatccggag tcgtcctatt ctaagaacga ggagatagag tctttagagc    2100
agtttcatat ggcaacggca gattcgttaa ttcgtaagca gatgagctcg attgtgtaca    2160
cgggtccgat taaagttcag caaatgaaaa actttatcga tagcctggta gcatcactat    2220
ctgctgcggt gtcgaatctc gtcaagatcc tcaaagatac agctgctatt gaccttgaaa    2280
cccgtcaaaa gtttggagtc ttggatgttg catctaggaa gtggttaatc aaaccaacgg    2340
ccaagagtca tgcatggggt gttgttgaaa cccacgcgag gaagtatcat gtggcgcttt    2400
tggaatatga tgagcagggt gtggtgacat cgatgattg gagaagagta gctgtcagct    2460
ctgagtctgt tgtttattcc gacatggcga aactcagaac tctgcgcaga ctgcttcgaa    2520
acggagaacc cgatgtcagt agcgcaaagg ttgttcttgt ggacggagtt ccgggctgtg    2580
ggaaaaccaa agaaattctt tccagggtta attttgatga agatctaatt ttagtacctg    2640
ggaagcaagc cgcggaaatg atcagaagac gtgcgaattc ctcagggatt attgtggcca    2700
cgaaggacaa cgttaaaacc gttgattctt tcatgatgaa ttttgggaaa agacacagct    2760
gtcagttcaa gaggttattc attgatgaag ggttgatgtt gcatactggt tgtgttaatt    2820
ttcttgtggc gatgtcattg tgcgaaattg catatgttta cggagacaca cagcagattc    2880
catacatcaa tagagtttca ggattcccgt accccgccca ttttgccaaa ttggaagttg    2940
acgaggtgga gacacgcaga actactctcc gttgtccagc cgatgtcaca cattatctga    3000
acaggagata tgagggcttt gtcatgagca cttcttcggt taaaaagtct gtttcgcagg    3060
agatggtcgg cggagccgcc gtgatcaatc cgatctcaaa acccttgcat ggcaagatcc    3120
tgacttttac ccaatcggat aaagaagctc tgctttcaag agggtattca gatgttcaca    3180
ctgtgcatga agtgcaaggc gagacatact ctgatgtttc actagttagg ttaacccca    3240 caccagtctc catcattgca ggagacagcc cacatgtttt ggtcgcattg tcaaggcaca    3300
cctgttcgct caagtactac actgttgtta tggatccttt agttagtatc attagagatc    3360
tagagaaact tagctcgtac ttgttagata tgtataaggt cgatgcagga acacaatagc    3420
aattacagat tgactcggtg ttcaaaggtt ccaatctttt tgttgcagcg ccaaagactg    3480
gtgatatttc tgatatgcag ttttactatg ataagtgtct cccaggcaac agcaccatga    3540
tgaataattt tgatgctgtt accatgaggt tgactgacat tcattgaat gtcaaagatt    3600 gcatattgga tatgtctaag tctgttgctg cgcctaagga tcaaatcaaa ccactaatac    3660
ctatggtacg aacggcggca gaaatgccac gccagactgg actattggaa atttagtgg    3720 cgatgattaa aaggaacttt aacgcacccg agttgtctgg catcattgat attgaaaata    3780
ctgcatcttt agttgtagat aagtttttg atagttattt gcttaaagaa aaagaaaac    3840 caaataaaaa tgtttctttg ttcagtagag agtctctcaa tagatggtta gaaaagcagg    3900
aacaggtaac aataggccag ctcgcagatt ttgattttgt agatttgcca gcagttgatc    3960
agtacagaca catgattaaa gcacaaccca agcaaaaatt ggacacttca atccaaacgg    4020
agtacccggc tttgcagacg attgtgtacc attcaaaaaa gatcaatgca atatttggcc    4080
cgttgtttag tgagcttact aggcaattac tggacagtgt tgattcgagc agattttgt    4140 ttttcacaag aaagacacca gcgcagattg cggatttctt cggagatctc gacagtcatg    4200
tgccgatgga tgtcttggag ctggatatat caaaatacga caaatctcag aatgaattcc    4260
actgtgcagt agaatacgag atctggcgaa gattgggttt tgaagacttc ttgggagaag    4320
tttggaaaca agggcataga aagaccaccc tcaaggatta taccgcaggt ataaaaactt    4380
```

-continued

```
gcatctggta tcaaagaaag agcggggacg tcacgacgtt cattggaaac actgtgatca    4440
ttgctgcatg tttggcctcg atgcttccga tggagaaaat aatcaaagga gccttttgcg    4500
gtgacgatag tctgctgtac tttccaaagg gttgtgagtt tccggatgtg caacactccg    4560
cgaatcttat gtggaatttt gaagcaaaac tgtttaaaaa acagtatgga tacttttgcg    4620
gaagatatgt aatacatcac gacagaggat gcattgtgta ttacgatccc ctaaagttga    4680
tctcgaaact tggtgctaaa cacatcaagg attgggaaca cttggaggag ttcagaaggt    4740
ctctttgtga tgttgctgtt tcgttgaaca attgtgcgta ttacacacag ttggacgacg    4800
ctgtatggga ggttcataag accgcccctc caggttcgtt tgtttataaa agtctggtga    4860
agtatttgtc tgataaagtt cttttttagaa gtttgtttat agatggctct agttgttaaa    4920
ggaaaagtga atatcaatga gtttatcgac ctgacaaaaa tggagccgat cttaccgtcg    4980
atgtttaccc ctgtaaagag tgttatgtgt tccaaagttg ataaaataat ggttcatgag    5040
aatgagtcat tgtcagaggt gaaccttctt aaaggagtta agcttattga tagtggatac    5100
gtctgtttag ccggtttggt cgtcacgggc gagtggaact tgcctgacaa ttgcagagga    5160
ggtgtgagcg tgtgtctggt ggacaaaagg atggaaagag ccgacgaggc cactctcgga    5220
tcttactaca cagcagctgc aaagaaaaga tttcagttca aggtcgttcc caattatgct    5280
ataaccaccc aggacgcgat gaaaaacgtc tggcaagttt tagttaatat tagaaatgtg    5340
aagatgtcag cgggtttctg tccgcttttct ctggagtttg tgtcggtgtg tattgtttat    5400
agaaataata taaaattagg tttgagagag aagattacaa acgtgagaga cggagggccc    5460
atggaactta cagaagaagt cgttgatgag ttcatggaag atgtccctat gtcgatcagg    5520
cttgcaaagt ttcgatctcg aaccggaaaa aagagtgatg tccgcaaagg aaaaatagt    5580 agtaatgatc ggtcagtgcc gaacaagaac tatagaaatg ttaaggattt tggaggaatg    5640
agttttaaaa agaataattt aatcgatgat gattcggagg ctactgtcgc cgaatcggat    5700 tcgtttttaaa tacgctcgag atcaatcatc catctccgaa gtgtgtctgc agcatgcagg    5760
tgctgaacac catggtgaac aaacacttct tgtcccttttc ggtcctcatc gtcctccttg    5820
gcctctcctc caacttgaca gccgggcaag tcctgtttca gggattcaac tgggagtcgt    5880
ggaaggagaa tggcgggtgg tacaacttcc tgatgggcaa ggtggacgac atcgccgcag    5940
ccggcatcac ccacgtctgg ctccctccgc cgtctcactc tgtcggagag caaggctaca    6000
tgcctgggcg gctgtacgat ctggacgcgt ctaagtacgg caacgaggcg cagctcaagt    6060
cgctgatcga ggcgttccat ggcaagggcg tccaggtgat cgccgacatc gtcatcaacc    6120
accgcacggc ggagcacaag gacggccgag gcatctactg cctcttcgag ggcgggacgc    6180
ccgactcccg cctcgactgg ggcccgcaca tgatctgccg cgacgacccc tacggcgatg    6240
gcaccggcaa cccggacacc ggcgccgact cgccgccgc gccggacatc gaccacctca    6300
acaagcgcgt ccagcgggag ctcattggct ggctcgactg gctcaagatg gacatcggct    6360
tcgacgcgtg gcgcctcgac ttcgccaagg gctactccgc cgacatggca aagatctaca    6420
tcgacgccac cgagccgagc ttcgccgtgg ccgagatatg gacgtccatg gcgaacggcg    6480
gggacggcaa gccgaactac gaccagaacg cgcaccggca ggagctggtc aactgggtcg    6540
atcgtgtcgg cggcgccaac agcaacggca cggcgttcga cttcaccacc aagggcatcc    6600
tcaacgtcgc cgtggagggc gagctgtggc gcctccgcgg cgaggacggc aaggcgcccg    6660
gcatgatcgg tgtggtgccg gccaaggcga cgacctttcgt cgacaaccac gacaccggct    6720
cgacgcagca cctgtggccg ttcccctccg acaaggtcat gcagggctac gcatacatcc    6780
```

```
tcacccaccc cggcaaccca tgcatcttct acgaccattt cttcgattgg ggtctcaagg    6840
aggagatcga gcgcctggtg tcaatcagaa accggcaggg gatccacccg gcgagcgagc    6900
tgcgcatcat ggaagctgac agcgatctct acctcgcgga gatcgatggc aaggtgatca    6960
caaagattgg accaagatac gacgtcgaac acctcatccc cgaaggcttc caggtcgtcg    7020
cgcacggtga tggctacgca atctgggaga aaatctgacc taggctcgca aagtttcgaa    7080
ccaaatcctc aaaaagaggt ccgaaaaata ataataattt aggtaagggg cgttcaggcg    7140
gaaggcctaa accaaaaagt tttgatgaag ttgaaaaaga gtttgataat ttgattgaag    7200
atgaagccga gacgtcggtc gcggattctg attcgtatta aatatgtctt actcaatcac    7260
ttctccatcg caatttgtgt ttttgtcatc tgtatgggct gaccctatag aattgttaaa    7320
cgtttgtaca aattcgttag gtaaccagtt tcaaacacag caagcaagaa ctactgttca    7380
acagcagttc agcgaggtgt ggaaaccttt ccctcagagc accgtcagat ttcctggcga    7440
tgtttataag gtgtacaggt acaatgcagt tttagatcct ctaattactg cgttgctggg    7500
ggcttttgat actaggaata gaataatcga agtagaaaac cagcagagtc cgacaacagc    7560
tgaaacgtta gatgctaccc gcagggtaga cgacgctacg gttgcaattc ggtctgctat    7620
aaataaatta gttaatgaac tagtaagagg tactggactg tacaatcaga atacttttga    7680
aagtatgtct gggttggtct ggacctctgc acctgcatct taaatgcata ggtgctgaaa    7740
tataaagttt gtgtttctaa aacacacgtg gtacgtacga taacgtacag tgtttttccc    7800
tggacttaaa tcgaagggta gtgtcttgga gcgcgcggag taaacatata tggttcatat    7860
atgtccgtag gcacgtaaaa aaagcgaggg attcgaattc ccccggaacc cccggttggg    7920
gcccag                                                               7926
```